US009429554B2

(12) United States Patent
Williams et al.

(10) Patent No.: US 9,429,554 B2
(45) Date of Patent: Aug. 30, 2016

(54) BORON AND LITHIUM ISOTOPIC METHOD FOR TRACING HYDROCARBONS AND THEIR BY-PRODUCTS

(71) Applicants: Lynda B. Williams, Tempe, AZ (US); Richard L. Hervig, Tempe, AZ (US)

(72) Inventors: Lynda B. Williams, Tempe, AZ (US); Richard L. Hervig, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 58 days.

(21) Appl. No.: 14/595,324

(22) Filed: Jan. 13, 2015

(65) Prior Publication Data
US 2015/0198577 A1    Jul. 16, 2015

Related U.S. Application Data

(60) Provisional application No. 61/926,665, filed on Jan. 13, 2014.

(51) Int. Cl.
*B01D 59/44* (2006.01)
*G01N 33/24* (2006.01)
(Continued)

(52) U.S. Cl.
CPC ........... *G01N 33/24* (2013.01); *H01J 49/0009* (2013.01); *H01J 49/142* (2013.01)

(58) Field of Classification Search
USPC .......... 250/253, 255, 281, 282, 526; 420/14, 420/64, 106, 121
See application file for complete search history.

(56) References Cited

U.S. PATENT DOCUMENTS 3,033,287 A * 5/1962 Bond ................... G01V 9/007
166/250.16
3,033,654 A * 5/1962 Slack ................... E21B 49/00
166/254.1
(Continued)

FOREIGN PATENT DOCUMENTS

GB          864225       3/1961
WO    2013/071188 A1    5/2013

OTHER PUBLICATIONS

L.B. Williams, A. Turner & R.L. Hervig, "Intracrystalline boron isotope partitioning in illite-smectite: Testing the geothermometer", American Mineralogist, vol. 92, pp. 1958-1965, 2007.
(Continued)

*Primary Examiner* — Bernard Souw
(74) *Attorney, Agent, or Firm* — Quarles & Brady LLP

(57) ABSTRACT

The invention relates to methods for determining the source of hydrocarbons presented in the pores of a host rock or found in contaminated groundwater. The method includes the steps of (a) determining a first isotopic composition of boron and/or lithium in one or more components within a potential source rock sample, such as kerogen, clay, or water; (b) determining a second isotopic composition of boron and/or lithium in the hydrocarbons found within the pores of a host rock sample or in contaminated groundwater; and (c) comparing the first and second isotopic compositions to determine whether the potential source rock is the source of the hydrocarbons within the pores of the host rock or in contaminated groundwater. The comparison is facilitated by using the isotope fractionation between the kerogen, clay, or water components and the bitumen component of the potential source rock, which allows one to predict the isotope composition of any hydrocarbons originating in the bitumen component of the source rock, based on the isotope composition of one of the other three phases. The method can be used to select host rock for extracting oil and other hydrocarbons, as well as in remediating groundwater contamination.

20 Claims, 32 Drawing Sheets

(51) Int. Cl.
*H01J 49/00* (2006.01)
*H01J 49/14* (2006.01)

(56) References Cited

U.S. PATENT DOCUMENTS

| | | | | |
|---|---|---|---|---|
| 8,558,166 | B2* | 10/2013 | Jiang | H01J 49/025 148/302 |
| 9,128,076 | B2* | 9/2015 | Lamberti | G01N 33/241 |
| 2006/0008916 | A1* | 1/2006 | Qiao | B01D 59/44 436/79 |
| 2013/0037707 | A1* | 2/2013 | Lamberti | G01N 33/241 250/282 |
| 2013/0091925 | A1 | 4/2013 | Darrah et al. | |
| 2014/0224001 | A1* | 8/2014 | Eisenhauer | G01V 5/06 73/61.55 |

OTHER PUBLICATIONS

L.B. Williams, J. Srodon, W.D. Huff, N. Clauer & R.L. Hervig, "Light element distributions (N, B, Li) in Baltic Basin bentonites record organic sources", Geochimica et Cosmochimica Acta, vol. 120, pp. 582-599, 2013.

L.B. Williams & R.L. Hervig, "Unconventional Isotopes in Unconventional Oil Shale", Abstracts of the Clay Minerals Society, 50th Annual Conference, p. 252, Oct. 10, 2013.

L.B. Williams & R.L. Hervig, "A SIMS Study of the Chemical Dynamics of Organic/Inorganic Interactions in Sedimentary Basins", Summary of FY2006 Geosciences Research, pp. 82-83, Dec. 2007.

N. Clauer, L.B. Williams & A.E. Fallick, "Genesis of nanometric illite crystals elucidated by light-element (hydrogen, lithium, boron and oxygen) isotope tracing, and K—Ar and Rb—Sr dating", Chemical Geology, vol. 383, pp. 26-50, 2014.

L.B. Williams, R.L. Hervig, M.E. Wieser & I. Hutcheon, "The influence of organic matter on the boron isotope geochemistry of the gulf coast sedimentary basin, USA", Chemical Geology, vol. 174, Issue 4, pp. 445-461, 2001.

L.B. Williams, R.L. Hervig, J.R. Holloway & I. Hutcheon, "Boron isotope geochemistry during diagenesis. Part I. Experimental determination of fractionation during illitization of smectite", Geochimica et Cosmochimica Acta, vol. 65, No. 11, pp. 1769-1782, 2001.

L.B. Williams, M.E. Wieser, J. Fennell, I. Hutcheon & R.L. Hervig, "Application of boron isotopes to the understanding of fluid-rock interactions in a hydrothermally stimulated oil reservoir in the Alberta Basin, Canada", Geofluids, vol. 1, pp. 229-240, 2001.

L.B. Williams & R.L. Hervig, "Boron isotope composition of coals: a potential tracer of organic contaminated fluids", Applied Geochemistry, vol. 19, pp. 1625-1636, 2004.

F. Scholz, C. Hensen, G.J. De Lange, M. Haeckel, V. Liebetrau, A. Meixner, A. Reitz & R.L. Romer, "Lithium isotope geochemistry of marine pore waters—Insights from cold seep fluids", Geochimica et Cosmochimica Acta, vol. 74, pp. 3459-3475, 2010.

A. Vengosh, K.G. Neumann, S. Juraske & R. Kasher, "Boron Isotope Application for Tracing Sources of Contamination in Groundwater", Environ. Sci. Technol., vol. 28, pp. 1968-1974, 1994.

N.R. Warner, T.H. Darrah, R.B. Jackson, R. Millot, W. Kloppmann & A. Vengosh, New Tracers Identify Hydraulic Fracturing Fluids and Accidental Releases from Oil and Gas Operations, Environ. Sci. Technol., vol. 48, pp. 12552-12560, 2014.

G. Panagopoulos, "Application of major and trace elements as well as boron isotopes for tracing hydrochemical processes: the case of Trifilia coastal karst aquifer, Greece", Environ Geol., vol. 58, pp. 1067-1082, 2009.

\* cited by examiner

BORON AND LITHIUM ISOTOPIC METHOD FOR TRACING HYDROCARBONS AND THEIR BY-PRODUCTS

CROSS-REFERENCE TO RELATED APPLICATIONS

This applications claims the benefit of U.S. provisional Application No. 61/926,665 filed on Jan. 13, 2014, which is incorporated by reference herein in its entirety.

STATEMENT REGARDING FEDERALLY SPONSORED RESEARCH

Not Applicable.

FIELD OF THE INVENTION

The invention generally relates to the field of geochemistry. Particularly, the invention relates to methods for determining the source of hydrocarbons and their by-products in an oil reservoir rock, and more particularly, the source of hydrocarbons presented in the nanopores of kerogen in potential source rock or in contaminated groundwater.

BACKGROUND OF THE INVENTION

This section is intended to introduce various aspects of the art and provide a framework to facilitate a better understanding of particular aspects of the present invention. While some aspects of the discussion in this section may be associated with exemplary embodiments of the present invention, the section should not be read necessarily as admissions of prior art.

Illitization (direct illite precipitation or smectite to illite conversion) is a widely used tracer for evaluating thermal evolution in volcano-sedimentary sequences during burial, metamorphic and tectonic events. Studies of light element isotopic geochemistry of illite-type nanocrystals have greatly improved our understanding of the illitization process (see Clauer, et. al., Chemical Geology 383 (2014): 26-50, which is incorporated by reference herein), and light element isotopes, such as $\delta^7Li$ and $\delta^{11}B$, have been shown to record specific paleofluid changes during illite crystal growth (see Williams, et. al., Geochimica et Cosmochimica Acta 120 (2013): 582-599, which is incorporated by reference herein).

In illite-smectite (I-S), Li substitutes in octahedral sites and B substitutes in tetrahedral sites (see FIG. 1A). In smectite, B and Li may also reside in the interlayers; however, the interlayer adsorbed contaminants may be removed to obtain consistent results for I-L. Over the past decade, fractionation curves between illite and water have been determined empirically, experimentally and theoretically for both lithium (FIG. 1B) and boron (FIG. 1C) isotopic fractionation.

The production of oil from shales has risen dramatically since 2010, when the price of oil reached $100/barrel. A particularly rich source of oil is the lower Bakken shale, which extends from western North Dakota into eastern Montana and up north into Canada. Lower Bakken shale is primarily illitic (72% illite-smectite), but also includes other components, such as quartz (15%), pyrite (7%), K-feldspar (3%), dolomite (2%), and plagioclase (1%).

Several regions of the Bakken shale are rich in organic compounds. In addition to the mineral components, such oil shales contain kerogen, a matrix made of largely insoluble, high molecular weight hydrocarbons, and bitumen, which is the source of the lower molecular weight organic solvent-soluble hydrocarbons that make up shale oil.

The oil producing potential of oil shale increases as the kerogen matrix thermally matures from the immature to the mature state (peak oil), and then decreases as the kerogen advances to an overmature and unproductive state. However, in some cases, an overmature kerogen matrix may host a substantial reservoir of extractable and commercially valuable hydrocarbons. Because of the thermal maturity of the kerogen matrix, such hydrocarbons are likely not sourced from the host rock, but have likely migrated from non-local bitumens.

Optimizing resource recovery while minimizing environmental impact are primary goals when extracting oil from oil shales. To identify optimal targets for enhanced oil recovery, it would be helpful to be able to accurately identify the source of hydrocarbons residing in the pores of a given host rock. For example, if the hydrocarbons in the pores of an overmature kerogen matrix can be shown to come from a mature (i.e., peak oil) source, extraction of the hydrocarbons may be commercially worthwhile, despite the overmature (i.e., unproductive) status of the host rock. Furthermore, accurate identification of the source of hydrocarbon contamination of groundwater can be used to monitor and remediate such contamination.

Conventional methods for linking bitumen and other hydrocarbon byproducts to their source rock include using a variety of organic biomarkers as source tracers. Many of these biomarkers are redox-sensitive, and tracing them often requires specialized and complex organic chemical analyses. Thus, there is a need in the art for a method of tracing hydrocarbons in a host rock to the original source rock that is not redox-sensitive, and that is independent of any organic compounds present in the hydrocarbons. Such a method could be used to identify areas for most productive hydraulic fracturing, and to promote environmentally responsible production of oil and gas.

SUMMARY OF THE INVENTION

The inventors recently discovered that that boron (B) and lithium (Li) partition into the bitumen phase of hydrocarbon source rocks as kerogen is thermally matured, where the bitumen is enriched in the heavy isotope of these elements while the kerogen and clays in the source rock are enriched in the light isotopes. It was further found that the isotopic fractionation is a function of thermal maturity. Based on these discoveries, the inventors developed a calibration curve for the fractionation of these isotopes between kerogen-water, clay-water and bitumen-water. The inventors envision that this analytical method can provide a useful tool to link bitumen (and other hydrocarbon by-products) to their source rock. Unlike previously used methods of linking hydrocarbons in host rock to its source rock, the stable isotopes of the inorganic tracers, boron and lithium, are not sensitive to oxidation and the sample redox conditions will not alter the isotopic ratios of the inorganic elements, so the measurement can be more easily interpreted.

For example, in some embodiments of the present invention, the analysis of isotopic boron and lithium can be done in situ on polished rock samples using secondary ion mass spectrometry (SIMS) or on isolates of the phases of interest (minerals, kerogen, bitumen). Thus, the analytical process can readily determine isotopic compositions of silicate or carbon based solid phases and further be used to identify whether the bitumen is in equilibrium with the host kerogen matrix or has migrated from another source. Using the new calibrated isotope fractionation between kerogen and bitumen, the isotopic composition of the source kerogen will be known and therefore the source region can be identified by separate analysis of core samples. The method can also be used to monitor potential mixing of hydraulic fracturing by-products with local groundwater.

Boron and lithium are found in elevated concentrations (100s ppm) in conventional oilfield brines, and appear to be released from kerogen along with hydrocarbons (HC); oil and gas. The isotopic composition of kerogen-derived B and Li is enriched in the light isotope relative to most minerals and waters in earth's crust. Therefore, three samples of Bakken shale (lower member) representing immature (Ro=0.5), mature (Ro~1.0) and overmature (Ro=3.0) regions of the basin were studied for baseline data on the elemental abundance and isotopic exchange of these trace elements between kerogen and illite-smectite as the black shale matured thermally in this confined reservoir.

Using secondary ion mass spectrometry (SIMS), isotopic compositions of B and Li were measured on <2 μm clay fractions, dichloromethane extracted bitumen, and hydrogen fluoride isolated kerogen from the Bakken shale. In addition, core samples were analyzed by NanoSIMS to map the distribution of nanopores (4-200 nm) that form in the mature kerogen as HC are generated and migration occurs. Variations in H/C and O/C in nanopores were explored, to identify 'live-C' (thermally matured, migrated HC) in the matrix of 'dead-C' (remnant kerogen).

Results for the <2 μm clay fraction (organics removed) show a linear decrease in $\delta^{11}B$ (+7 to −12‰) and $\delta^7Li$ (+10 to −1‰) from immature to overmature shale (1σ errors<1‰). The kerogen $\delta^{11}B$ ranges from (−12 to −15‰) while $\delta^7Li$ decreases (−6 to −18‰) with increasing thermal maturity. These trends suggest kerogen is the source of isotopically light B and Li that substitute in illite during diagenesis. Bitumen $\delta^{11}B$ averages+3‰ and $\delta^7Li$ averages+10‰, showing no change with kerogen thermal maturity.

Knowing isotope fractionation factors for B and Li between illite and water and using the vitrinite reflectance values to estimate temperature, a calculation of the $\delta^{11}B$ and $\delta^7Li$ of water was made, assuming equilibrium. From this an estimate of isotope fractionations between the kerogen and water are calculated for B and Li as a function of temperature:

$$\text{For B: } 1000 \ln \alpha_{ker\text{-}water} = -28(1000/K) + 39; \text{ For Li:}$$
$$1000 \ln \alpha_{ker\text{-}water} = -8(1000/K) - 1.$$

There is a 30‰ range in B-isotope fractionation as B is released from kerogen over a temperature range of ~70-280° C., while Li-isotope fractionation changes by ~10‰. The large isotope fractionations over temperatures of HC generation make B and Li released from kerogen a viable tracer of mature HC related fluids. Elevated concentrations of light B and Li in shale nanopores may help to identify optimal targets for enhanced oil recovery.

DETAILED DESCRIPTION OF THE INVENTION

Figure 1A:
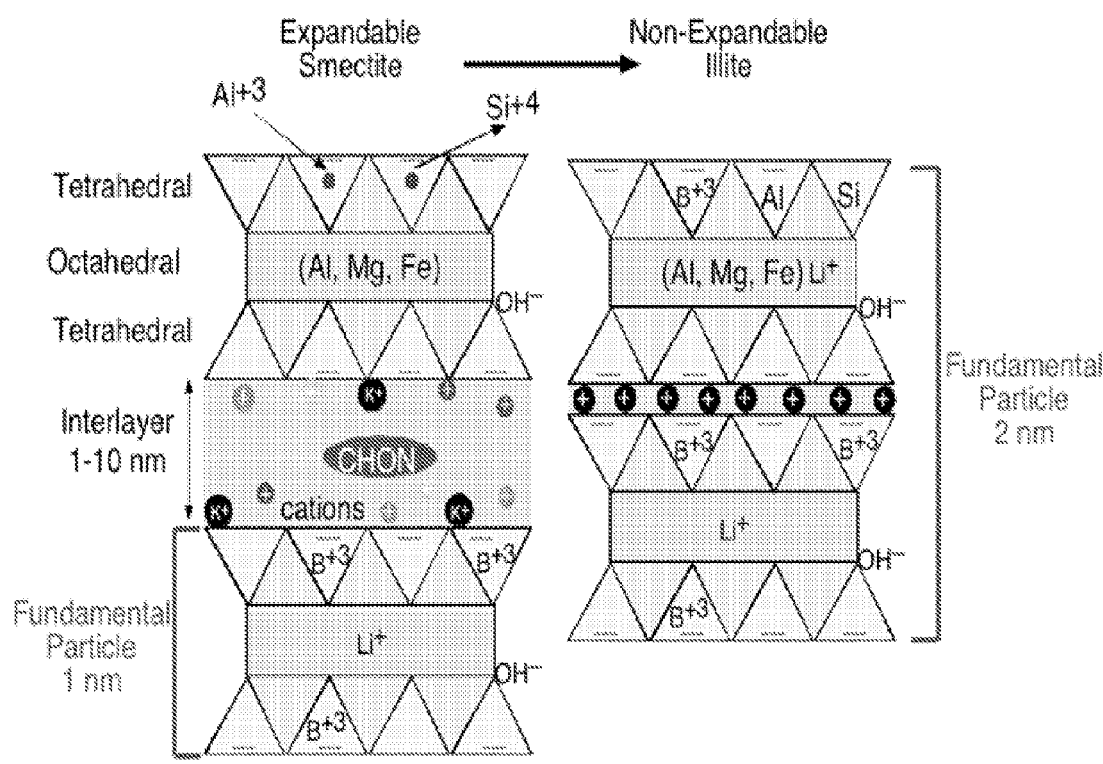
FIG. 1A is a schematic cross section of illite-smectite showing the location of B and Li. Li substitutes in octahedral sites and B substitutes in tetrahedral sites of illite.
Figure 1B:
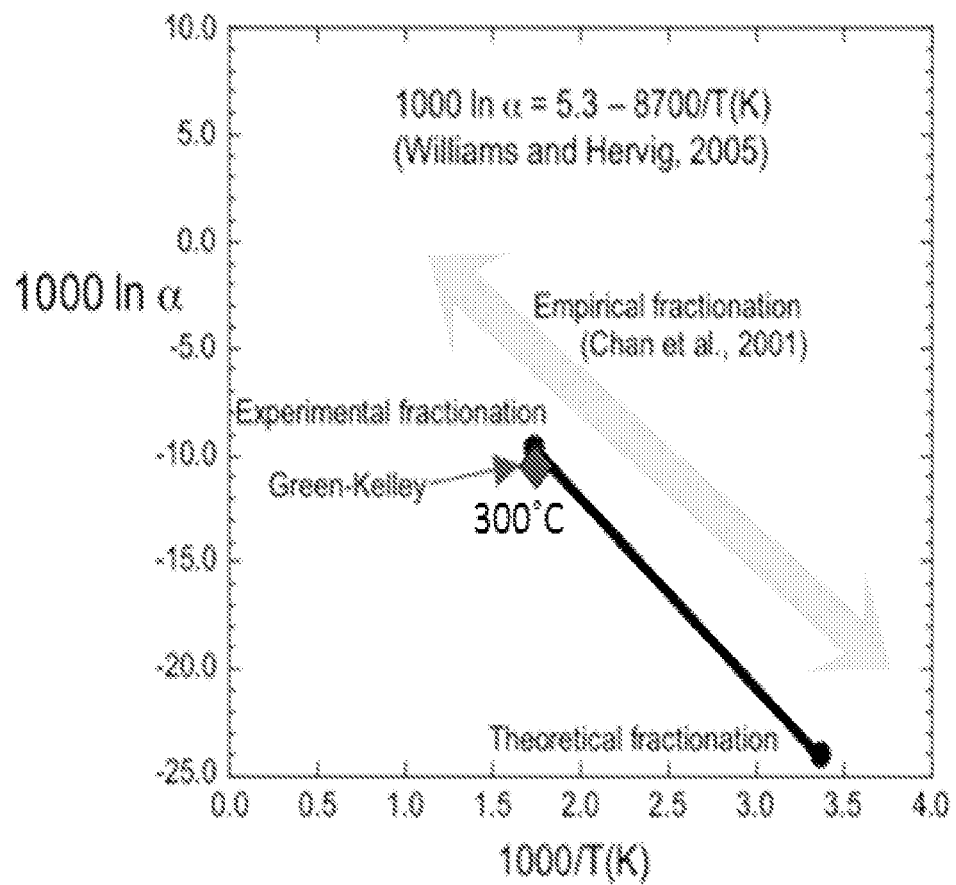
FIG. 1B shows illite-water isotope fractionation curves for lithium.
Figure 1C:
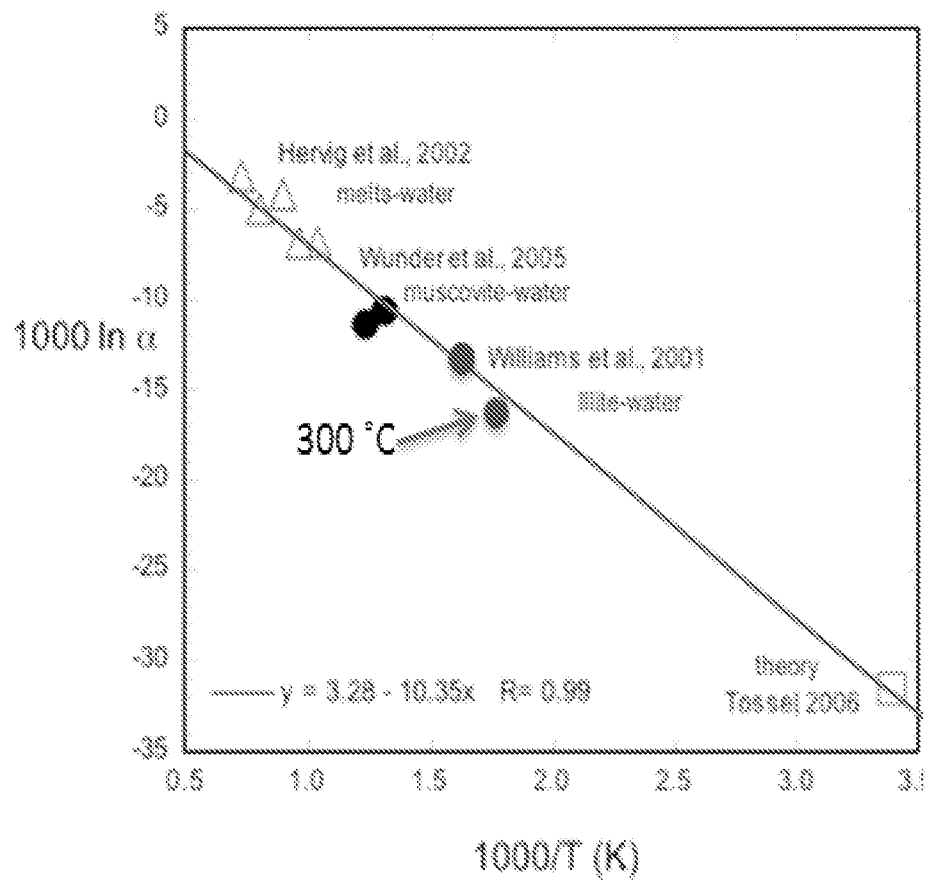
FIG. 1C shows an isotope fractionation curve for boron under pH conditions<7, where $B(OH)_3$ is the dominant aqueous B specie.

The present invention provides a method of identifying the nature and source of hydrocarbons in pores of kerogen from shale reservoirs. Specifically, the inventors have modeled the lithium and/or boron isotopic fractionation between the kerogen and bitumen phases of a potential source rock as a function of the temperatures derived from the kerogen thermal maturity. If the isotopic composition of the pore hydrocarbons (i.e., the bitumen phase) of the potential source rock is not as predicted based on the isotope fractionation model, then the bitumen is not from the potential source rock, and has migrated in from another source. Modeling different temperatures and/or source kerogen compositions may then reveal the source of migrated bitumen.

The kerogen composition of the potential source rock can be directly measured; however, isotope fractionation models using other source rock phases may also be used to determine the expected lithium and/or boron isotopic compositions of the bitumen phase. For example, a fractionation model may use the isotopic composition of boron and/or lithium in the clay (illite) surrounding the kerogen, or of the water in equilibrium with the clay.

A general indication that the local kerogen is the source of the bitumen in a black shale interval is when heavier isotopes of boron and/or lithium fractionate into the bitumen and lighter isotopes of boron and/or lithium fractionate into the clay or kerogen as predicted by the equilibrium isotope fractionation equation.

Accordingly, in a first aspect, this disclosure encompasses a method for identifying the source of hydrocarbons within the pores of a host rock. The method includes the steps of (a) determining a first isotopic composition of boron and/or lithium in one or more components within a potential source rock sample selected from the group consisting of kerogen, clay, and water; (b) determining a second isotopic composition of boron and/or lithium in the hydrocarbons within the pores of a host rock sample; and (c) comparing the first and second isotopic compositions to determine whether the potential source rock is the source of the hydrocarbons within the pores of the host rock.

In some embodiments, the host rock comprises kerogen, and the pores of the host rock sample are pores within the kerogen of the host rock sample.

In some embodiments, the host rock sample and the potential source rock sample are the same, and the method determines whether the bitumen within the host rock is the source of the hydrocarbons within the pores of the host rock.

In some embodiments, the comparison step (c) comprises using a relationship between the first isotopic composition and a third isotopic composition of boron and/or lithium within the bitumen phase of the potential source rock (i.e., the expected isotopic composition of the local bitumen). In some such embodiments, the potential source rock is identified as the source of the hydrocarbons within the pores of the host rock if the third isotopic composition is substantially similar to the second isotopic composition.

In some embodiments, the method further includes measuring the thermal maturity of the kerogen within the potential source rock sample. The relationship between the first isotopic composition and the third isotopic composition may be based in part on the thermal maturity of the kerogen within the potential source rock.

In some embodiments, the relationship between the first isotopic composition and the third isotopic composition is based at least in part on the boron isotope and/or lithium isotope fractionation between one or more of: (a) the kerogen and bitumen within the potential source rock; (b) the clay and bitumen within the potential source rock; or (c) the water and bitumen within the potential source rock. In some such embodiments, the relationship between the first isotopic composition and the third isotopic composition is further based at least in part on the boron isotope and/or lithium isotope fractionation between one or more of: (d) the clay and water within the potential source rock; or (e) the kerogen and water within the potential source rock.

In some embodiments, the relationship between the first isotopic composition and the third isotopic composition is based at least in part on an isotope fractionation curve or an isotope fractionation equation.

Some embodiments further include the step of using the identified source of the hydrocarbons in the pores of the host rock to determine whether to extract hydrocarbons from the host rock. In some such embodiments, the method further comprises the step of extracting hydrocarbons from the host rock. In some such embodiments, the step of extracting hydrocarbons from the source rock comprises drilling into the host rock and/or hydrofracturing the host rock.

In some embodiments, the host rock is a black shale, an oil shale, or a gas shale.

In some embodiments, the step of measuring the thermal maturity of the kerogen within the potential source rock sample is performed by determining vitrinite reflectance or by using other thermal indicators.

In some embodiments, step (a), step (b), or both are performed using mass spectrometry. In some such embodiments, nano secondary ion mass spectrometry (NanoSIMS) is used.

In a second aspect, the disclosure encompasses a method for identifying a source of hydrocarbon contaminants in groundwater. The method includes the steps of (a) determining a first isotopic composition of boron and/or lithium in one or more components within a potential source rock sample selected from the group consisting of kerogen, clay, and water; (b) determining a second isotopic composition of boron and/or lithium within the hydrocarbon contaminants in groundwater; and (c) comparing the first and second isotopic compositions to determine if the source rock is the source of the hydrocarbon contaminants.

In some embodiments, the potential source rock comprises oil shale.

In some embodiments, the comparison step (c) comprises using a relationship between the first isotopic composition and a third isotopic composition of boron and/or lithium within the bitumen phase of the potential source rock.

In some embodiments, the relationship between the first isotopic composition and the third isotopic composition is based at least in part on the boron isotope and/or lithium isotope fractionation between one or more of: (a) the kerogen and bitumen within the potential source rock; (b) the clay and bitumen within the potential source rock; or (c) the water and bitumen within the potential source rock.

The following paragraphs describe several exemplary embodiments of the present invention. These examples are offered for illustrative purposes only, and are not intended to limit the scope of the present invention in any way. Indeed, various modifications of the invention in addition to those shown and described herein will become apparent to those skilled in the art from these examples and fall within the scope of the appended claims.

The samples studied were from the Mississippian Bakken shale, which is one of the major oil shales discovered in North America. It is known that boron (B) and lithium (Li) are found in elevated concentrations (100s ppm) in conventional oilfield brines, and appear to be released from kerogen along with hydrocarbons (HC). The isotopic composition of kerogen-derived B and Li is enriched in the light isotope relative to most minerals and waters in earth's crust. Therefore, the inventors chose three samples of Bakken shale (lower member) representing immature (Ro=0.5–vitrinite reflectance), mature (near peak oil production) (Ro~1.0–vitrinite reflectance) and overmature (Ro=3.0–vitrinite reflectance) regions of the basin for the studies. The samples collected contained between 10-20% TOC. The baseline data on the elemental abundance and isotopic exchange of these trace elements between kerogen and illite-smectite type clay minerals were analyzed as the black shale matured thermally in this confined reservoir.

The cores of the most organic rich unit, the lower Bakken, were sampled. There are two intervals of organic rich shale, which average 11% total organic carbon (TOC).

Sample preparation used the following methods. For clays, (i) extraction of bitumen with dichloromethane (DCM); (ii) kerogen removed with hot bleach (pH 9.5) in triplicate; (iii) isolation of the <0.2 μm clay fraction by centrifugation and (iv) exchange of clays with NaCl (1N) to remove interlayer B & Li; (v) mannitol wash (0.1N mannitol) to remove surface adsorbed B & Li; and (vi) clays dried onto B-free glass slides, Au coated. For organics, (i) bitumen extracted with DCM, dried onto B & Li 'free' smectite; and (ii) kerogen extracted with HF (5N)—HCl (1N) (80° C.) in triplicate; washed with mannitol to remove surface contaminants. Thus, bitumen, kerogen and clay were isolated separately from the Bakken shale. Specifically, bitumen was extracted by using dichloromethane (DCM), kerogen was isolated by using hydrofluoric acid (HF), which dissolves silicates from the kerogen. Separately, clays were separated from the rock by disaggregation and centrifugation. Hot bleach treatments removed organics from the clay.

Figure 2A:
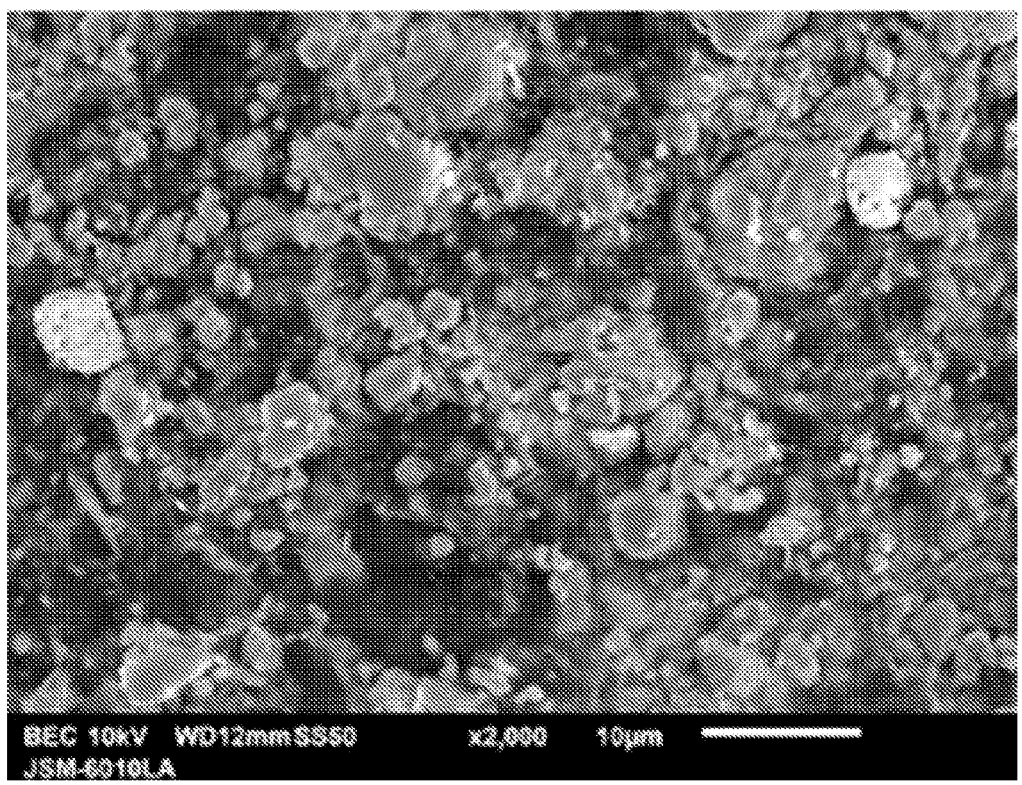
FIG. 2A is an image of a mechanically polished Bakken shale sample.
Figure 2B:
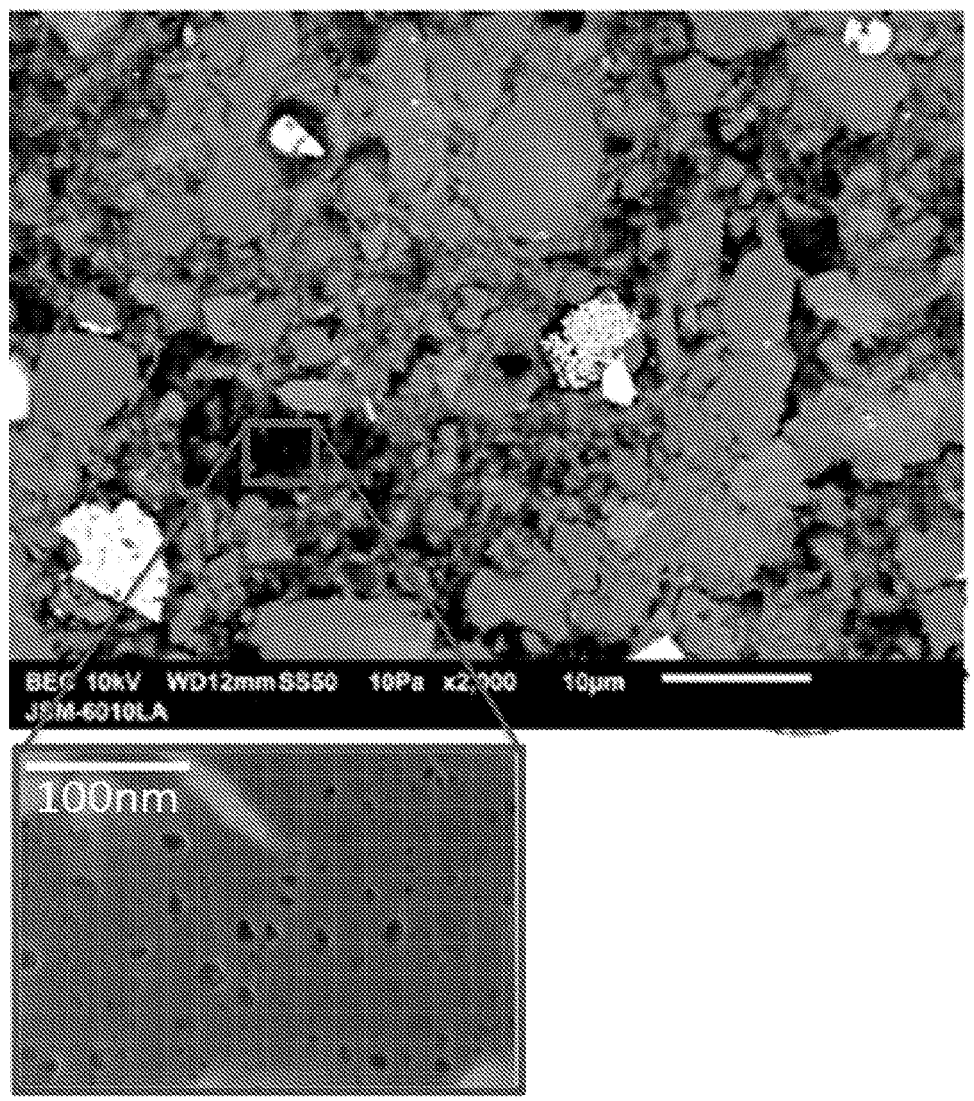
FIG. 2B is an image of a Bakken shale sample that has been polished using an Ar-ion beam. The inset is a further magnified image of the nanopores that are revealed in the kerogen. These nanopores are of keen interest to the oil industry, as they represent the channels where oil and gas has migrated out of the mature kerogen.
Figure 3A:
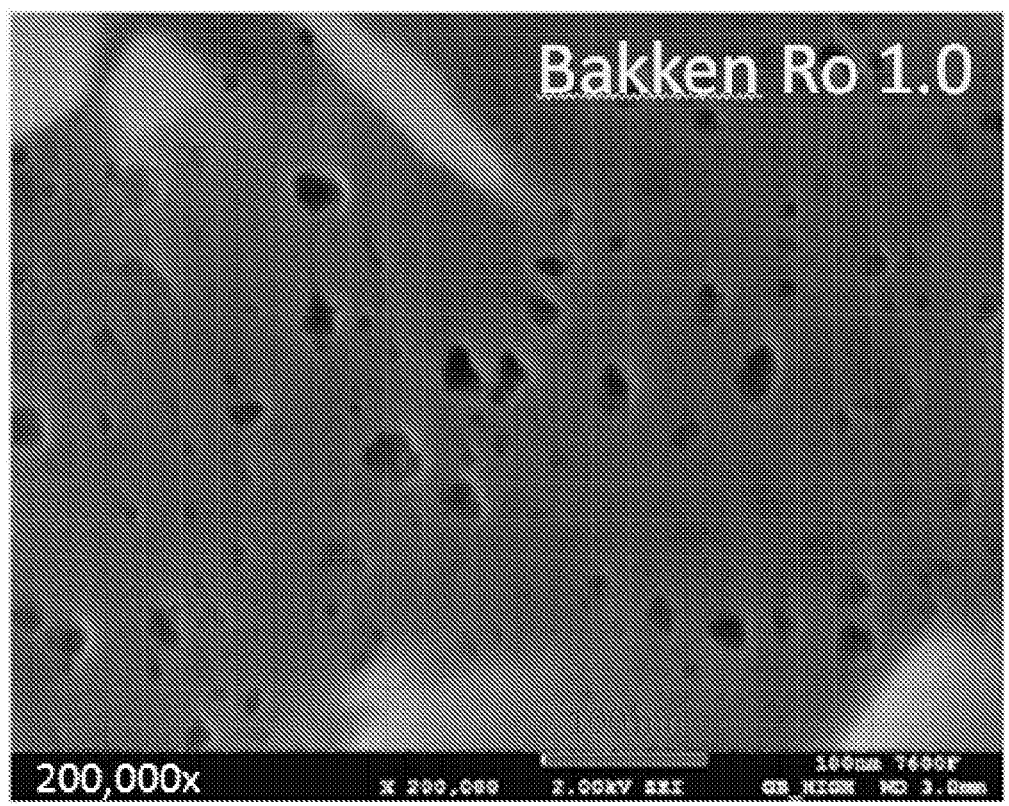
FIG. 3A is a 200,000× image showing pores in mature kerogen (Ro=1.0) from the Bakken.
Figure 3B:
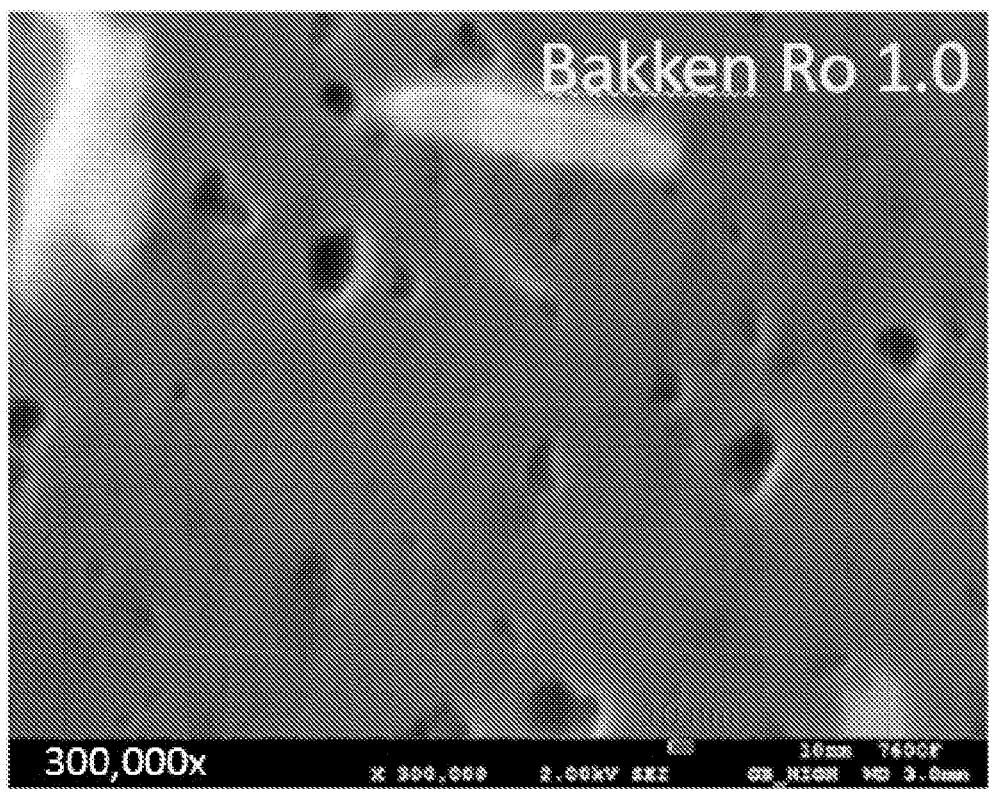
FIG. 3B is a 300,000× image showing pores in mature kerogen (Ro=1.0) from the Bakken.
Figure 3C:
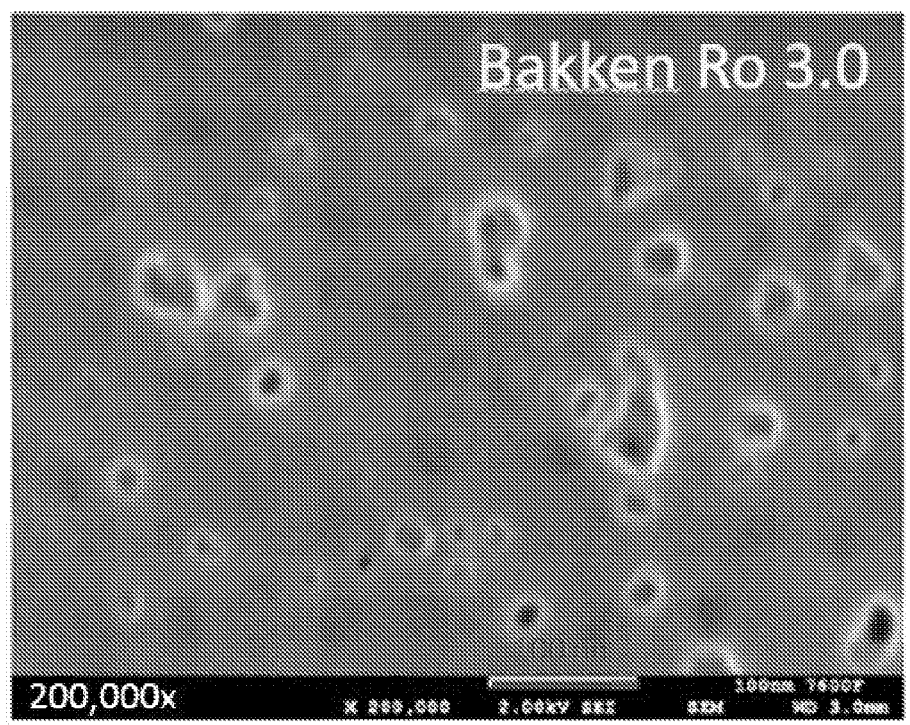
FIG. 3C is a 200,000× image showing pores in overmature kerogen (Ro=3.0) from the Bakken.
Figure 3D:
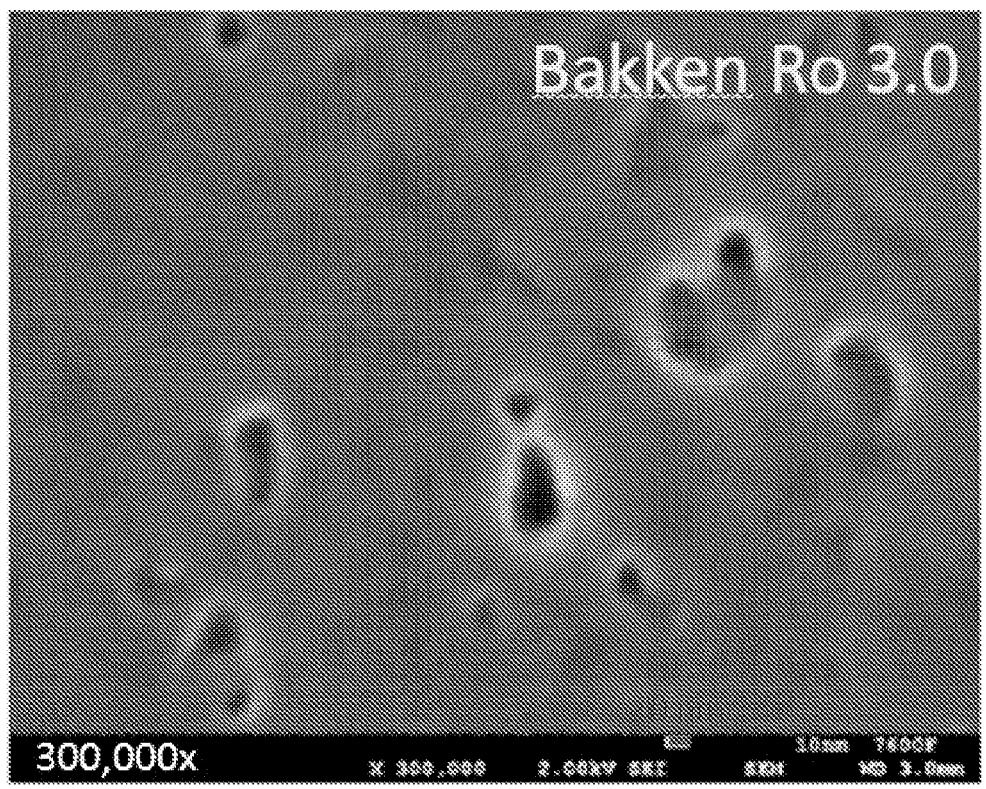
FIG. 3D is a 300,000× image showing pores in overmature kerogen (Ro=3.0) from the Bakken. Imaging in FIGS. 2B-3D was done by a representative from JEOL, to demonstrate the capability of the JEOL Ar-ion polisher.

As shown in FIG. 2A, mechanical polishing, even with a <1 μm grit, does not adequately polish shales. Instead the samples polished using an Ar-ion beam are ideal for surfaces with variable density, like kerogen and clays. This method of polishing reveals nanopores in the kerogen (FIG. 2B), which are of keen interest to the oil industry as they represent channels where the oil and gas has migrated out of the mature kerogen.

FIG. 3 illustrates images of the pores in the mature (FIGS. 3A and 3B) and overmature (FIGS. 3C and 3D) kerogen from the Bakken. The immature kerogen did not have nanopores. FIGS. 3A and 3C are 200 k magnification, and FIGS. 3B and 3D are 300 k magnification. It appeared that the pores increase in diameter with increasing thermal grade. Also, the darker grey patchy areas may indicate either different organic compounds in the kerogen or incipient pores.

Figure 4A:
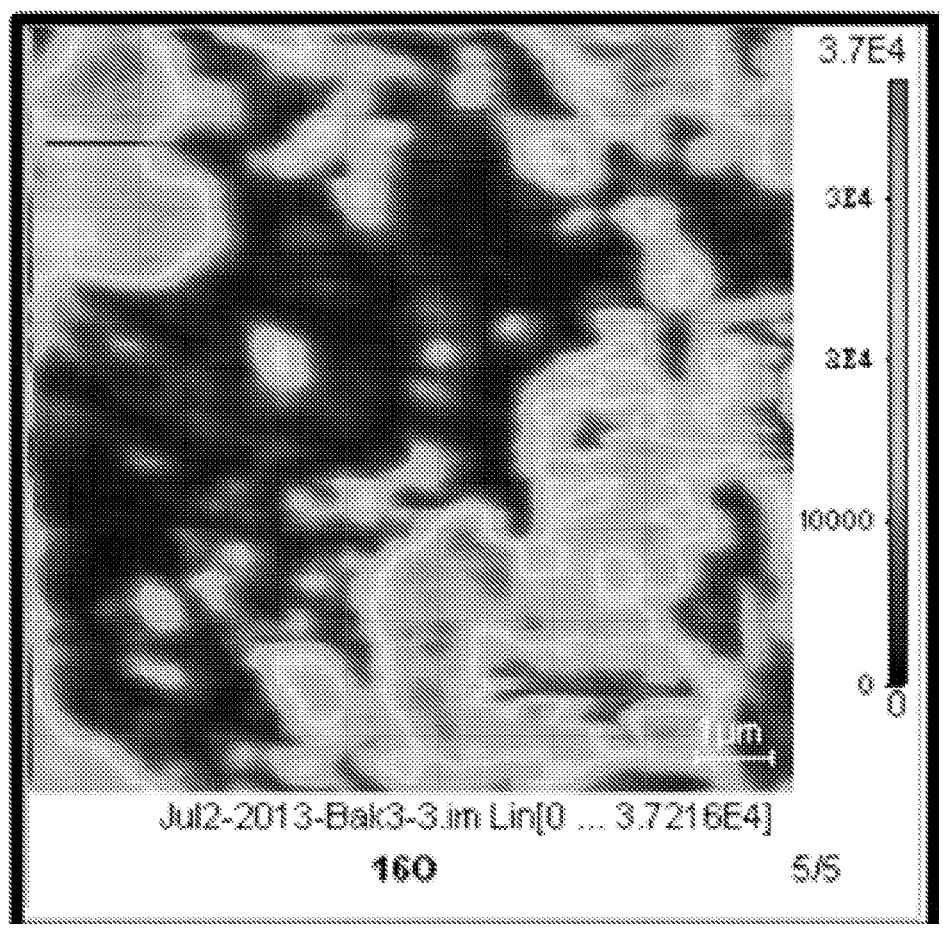
FIG. 4A is a 10 μm square NanoSIMS oxygen map of mature Bakken kerogen (Ro=3.0) nanopores obtained from Ar ion polished shale.
Figure 4B:
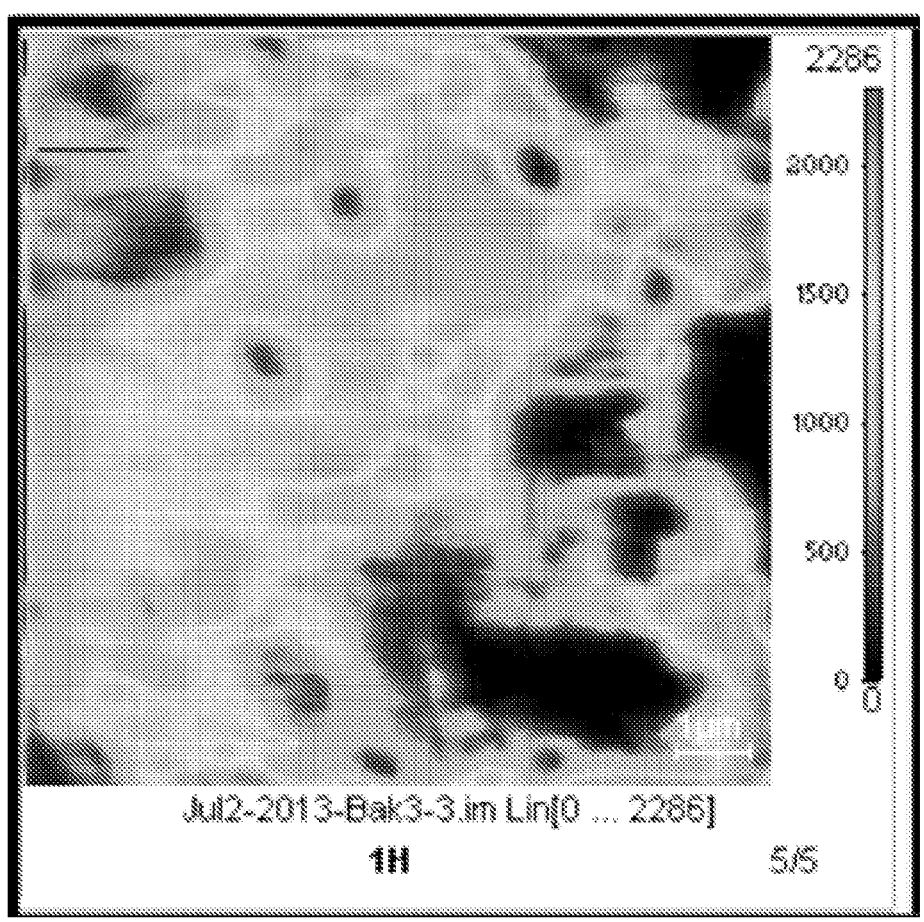
FIG. 4B is a 10 μm square NanoSIMS hydrogen map of mature Bakken kerogen (Ro=3.0) nanopores obtained from Ar ion polished shale.
Figure 4C:
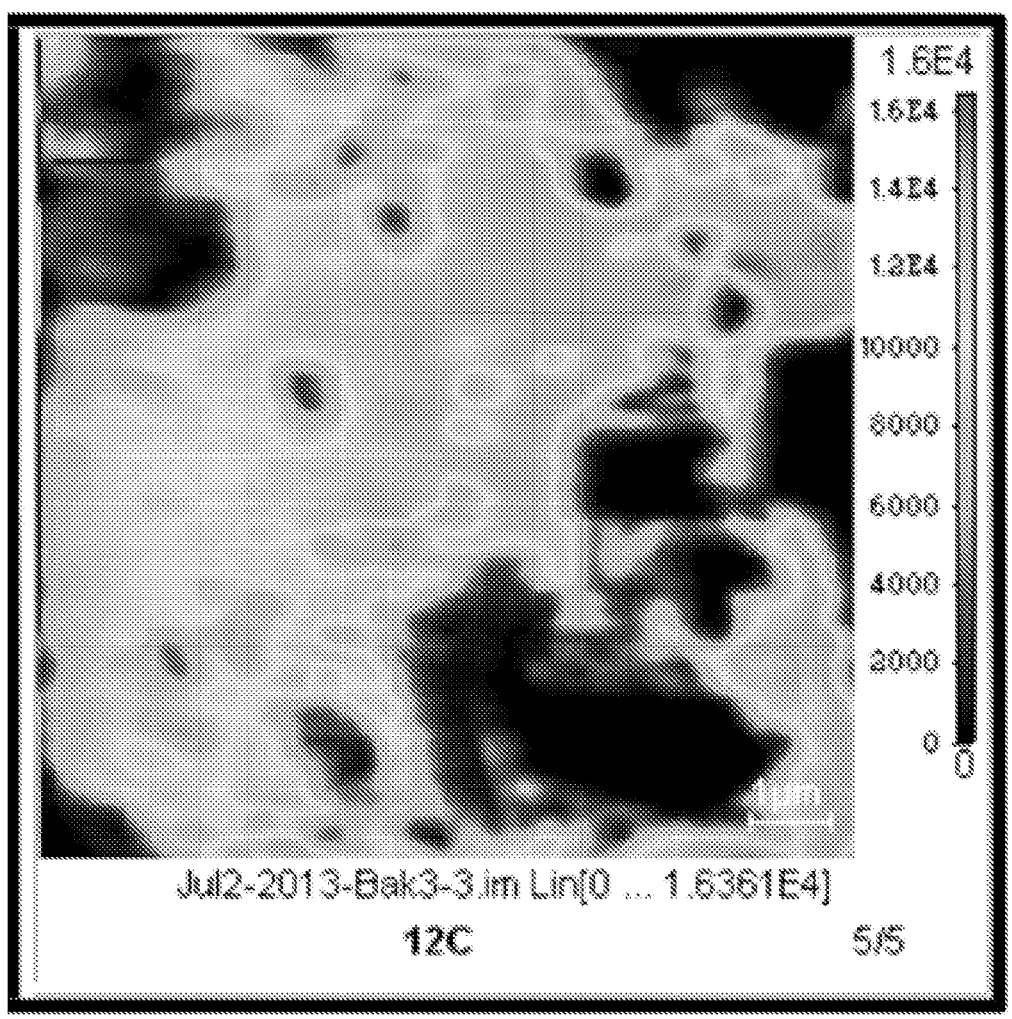
FIG. 4C is a 10 μm square NanoSIMS carbon map of mature Bakken kerogen (Ro=3.0) nanopores obtained from Ar ion polished shale.
Figure 4D:
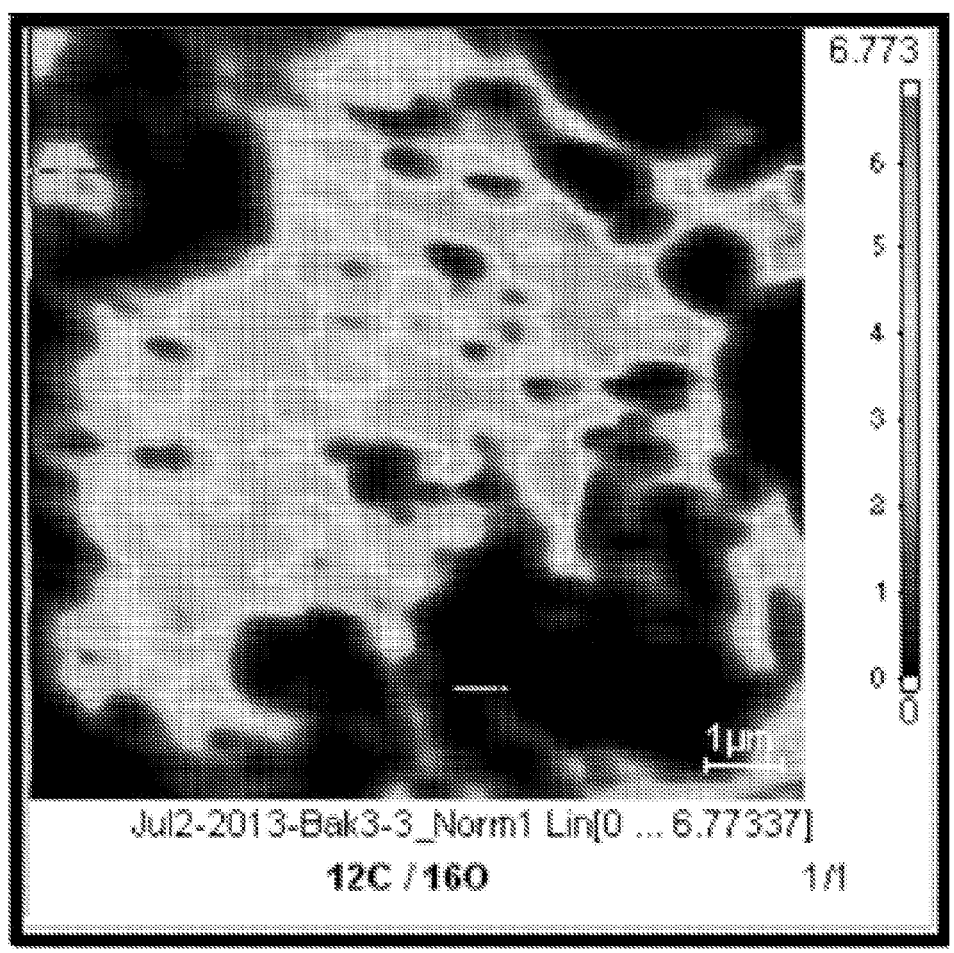
FIG. 4D is a 10 μm square NanoSIMS C/O map of mature Bakken kerogen (Ro=3.0) nanopores obtained from Ar ion polished shale. NanoSIMS images shown in FIGS. 4A-4D were taken by an imaging expert.

The core samples were further analyzed by NanoSIMS to map the distribution of nanopores (4-200 nm) that form in the mature kerogen as hydrocarbons are generated and migration occurs. In NanoSIMS, separation is not necessary as maps can be made on 10 μm areas with 50 to 100 nanometer resolution. Variations in H/C and O/C in nanopores were explored to identify live-C' (thermally matured, migrated HC) in the matrix of 'dead-C' (remnant kerogen). FIG. 4 shows 10 μm square maps of O (FIG. 4A), H (FIG. 4B) and C (FIG. 4C). FIG. 4D maps the ratio of C/O, which best shows the compositional differences between the matrix and material in the nanopores.

Figure 5A:
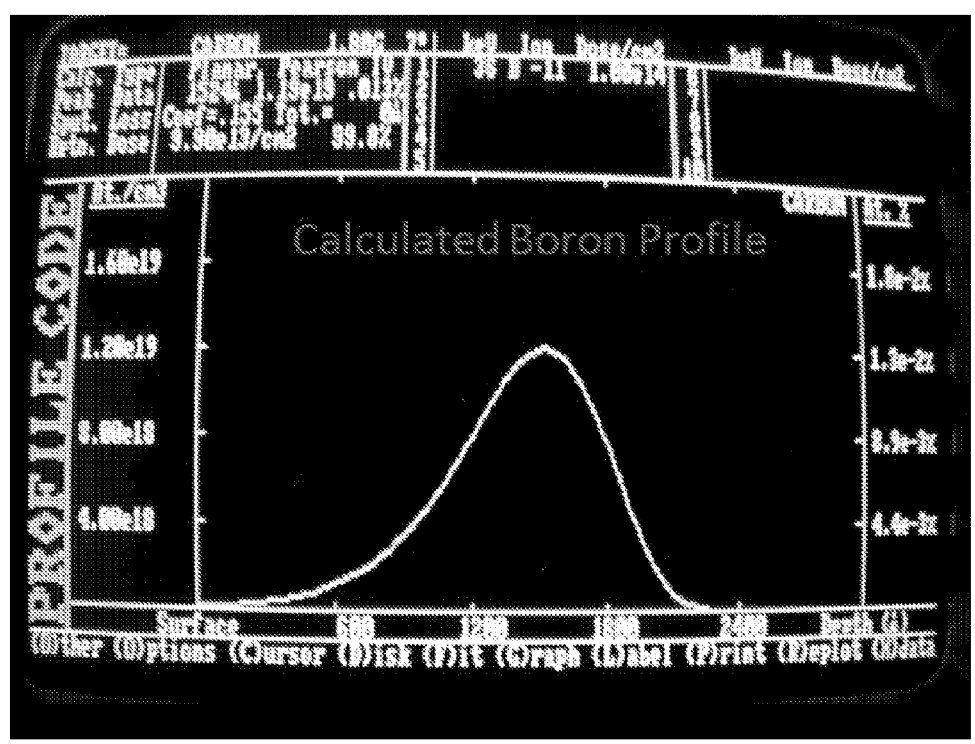
FIG. 5A is a calculated boron profile for boron implanted in a graphite matrix (density 1.8 g/cc) at 1000 ppm and a depth of 150 nm.
Figure 5B:
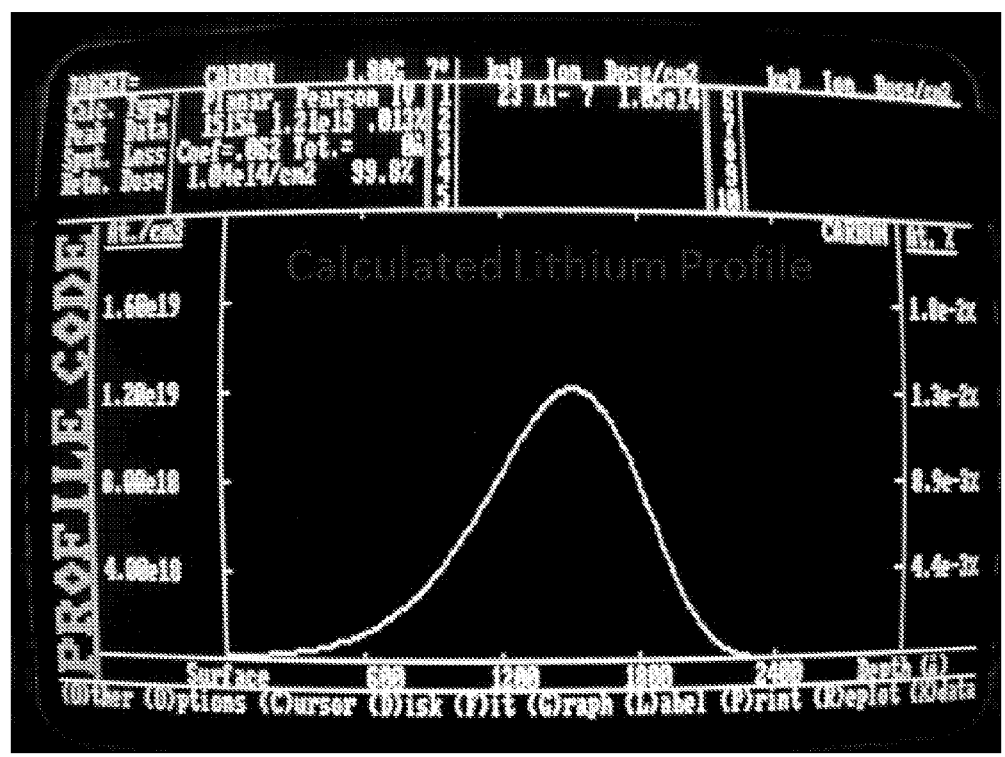
FIG. 5B is a calculated lithium profile for lithium implanted in a graphite matrix (density 1.8 g/cc) at 1000 ppm and a depth of 150 nm.

To calibrate the matrix effects on ion yields by SIMS, the inventors used the standard method in materials science to implant ions into a matrix (usually Si), with a known concentration at a known depth. These ion implants were done commercially to make a calibration for the isotopes of interest in a particular matrix. A variety of carbon matrices, a glassy carbon, single crystal carbon were implanted, and a NIST glass (SRM 612) with a known B and Li content, was chosen to test the implant accuracy. Boron and lithium were also implanted into Bakken kerogen to test the effect of the variable H-content on ion yields. In the calculated boron (FIG. 5A) and lithium (FIG. 5B) profiles, the calculations for the implant dose and energy were based on the density of the matrix, and the concentration of the implant (1000 ppm) and depth of the implant were selected to be 150 nanometers.

The inventors performed a 125 μm rastered depth profile into the implanted matrices. The primary ion beam is rastered over an area, removing atoms from the sample surface. Some of the particles removed are ionized and those charged particles can be extracted from the sample and moved into the secondary mass spectrometer where the ions are separated by mass, and then counted by an electron multiplier or Faraday cup.

Figure 6:
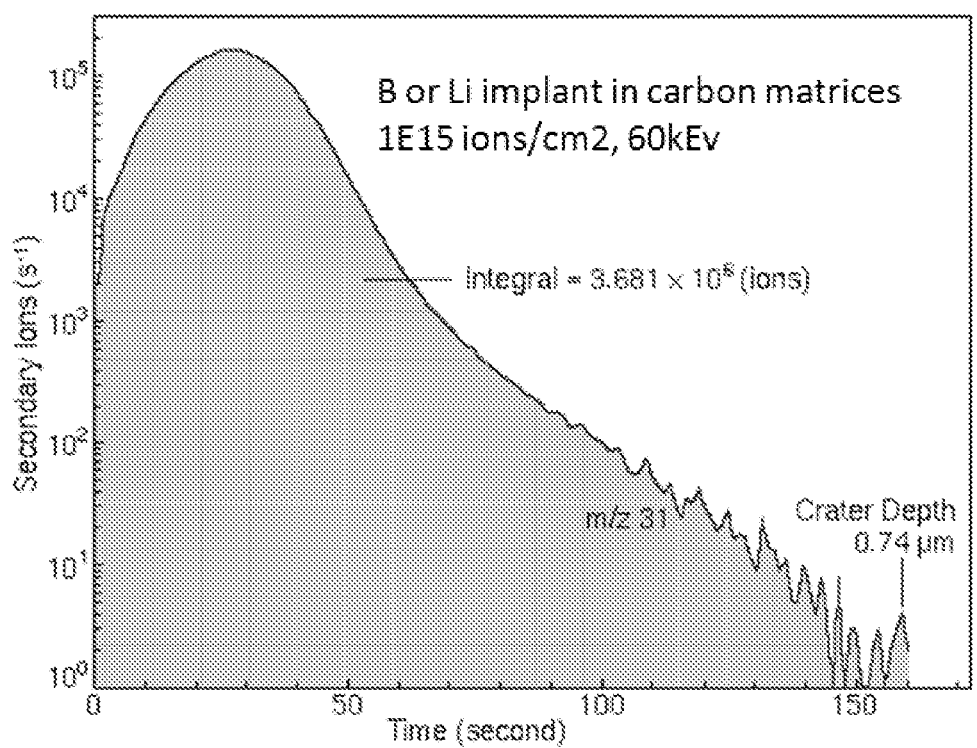
FIG. 6 is an exemplary depth profile showing ion yield as a function of time, which can be converted to a relative sensitivity factor (RSF).
Figure 7A:
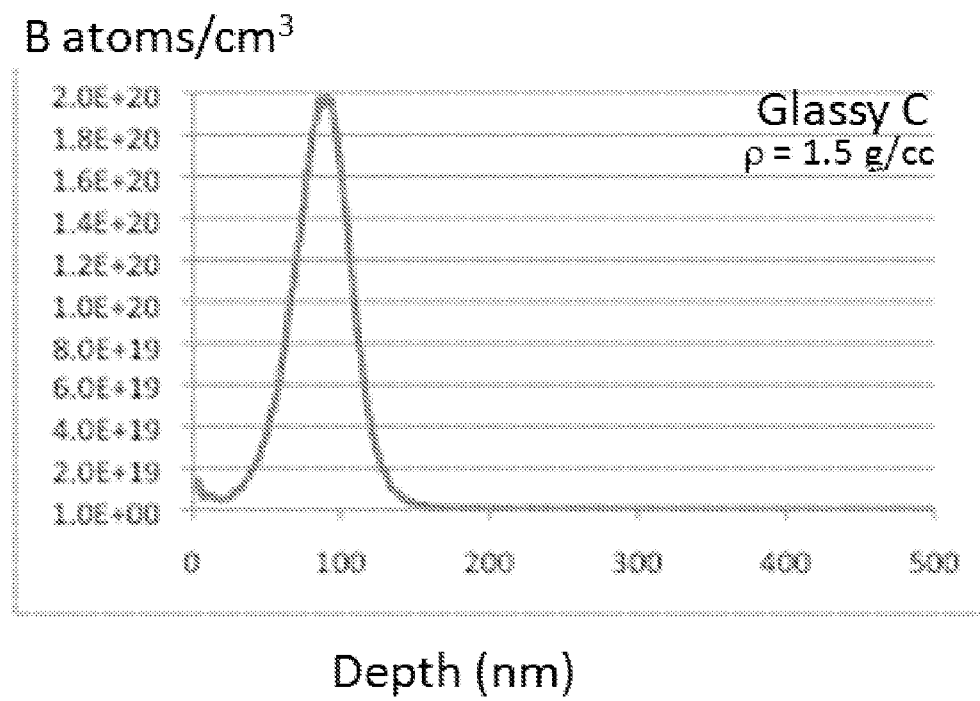
FIG. 7A is a measured boron implant profile using a glassy C matrix.
Figure 7B:
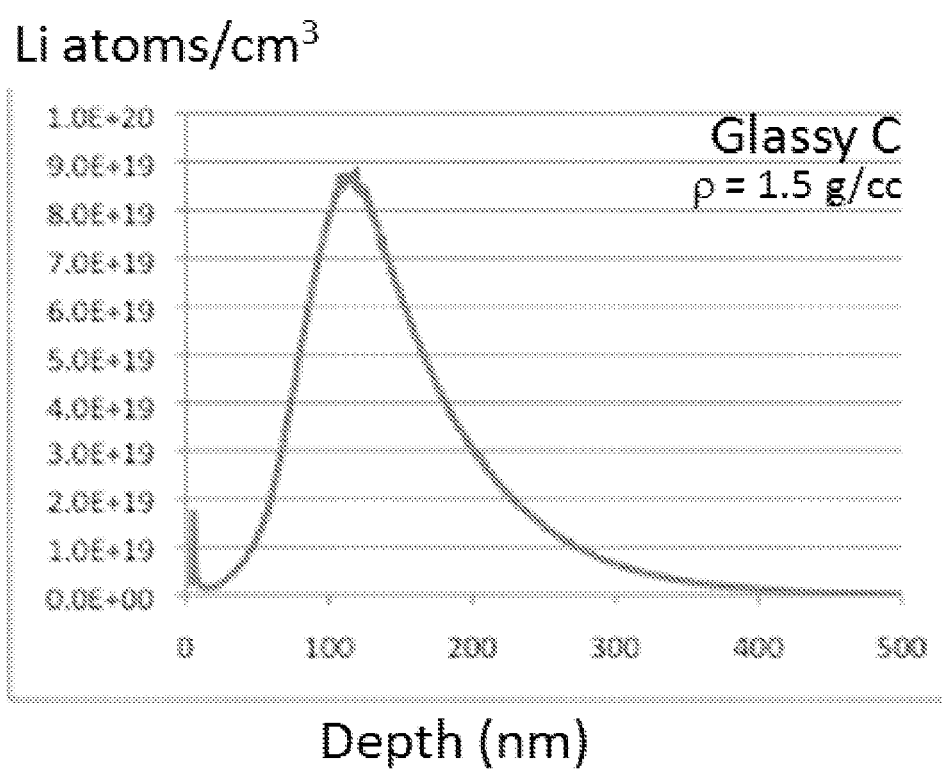
FIG. 7B is a measured lithium implant profile using a glassy C matrix.
Figure 7C:
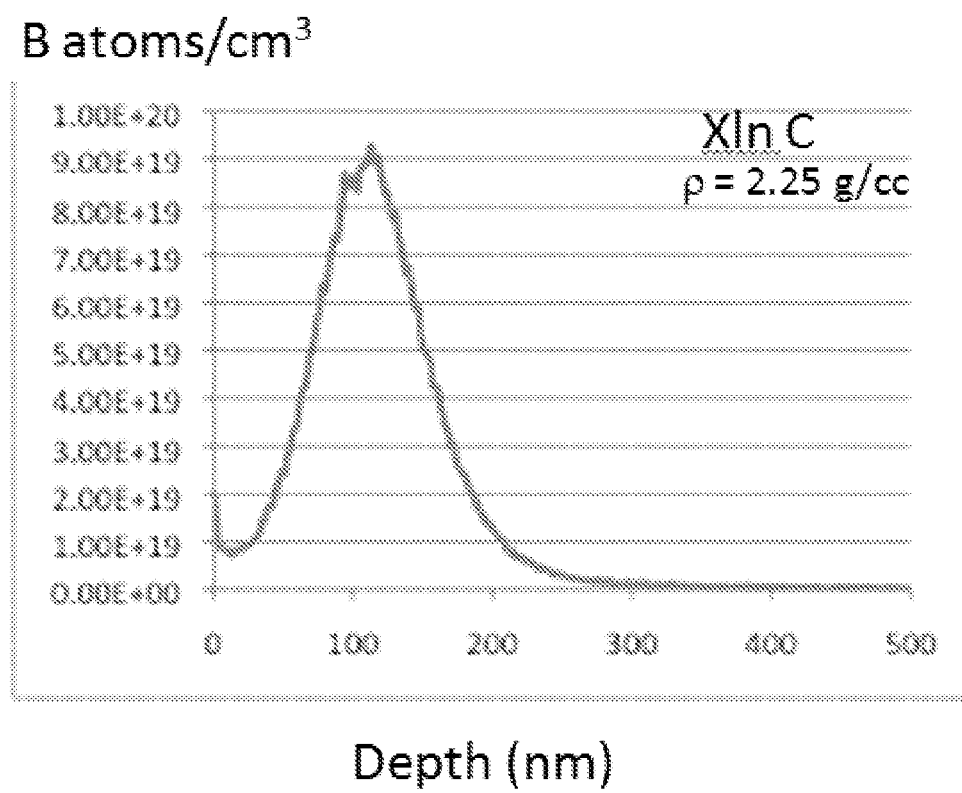
FIG. 7C is a measured boron implant profile using a single crystal C matrix.
Figure 7D:
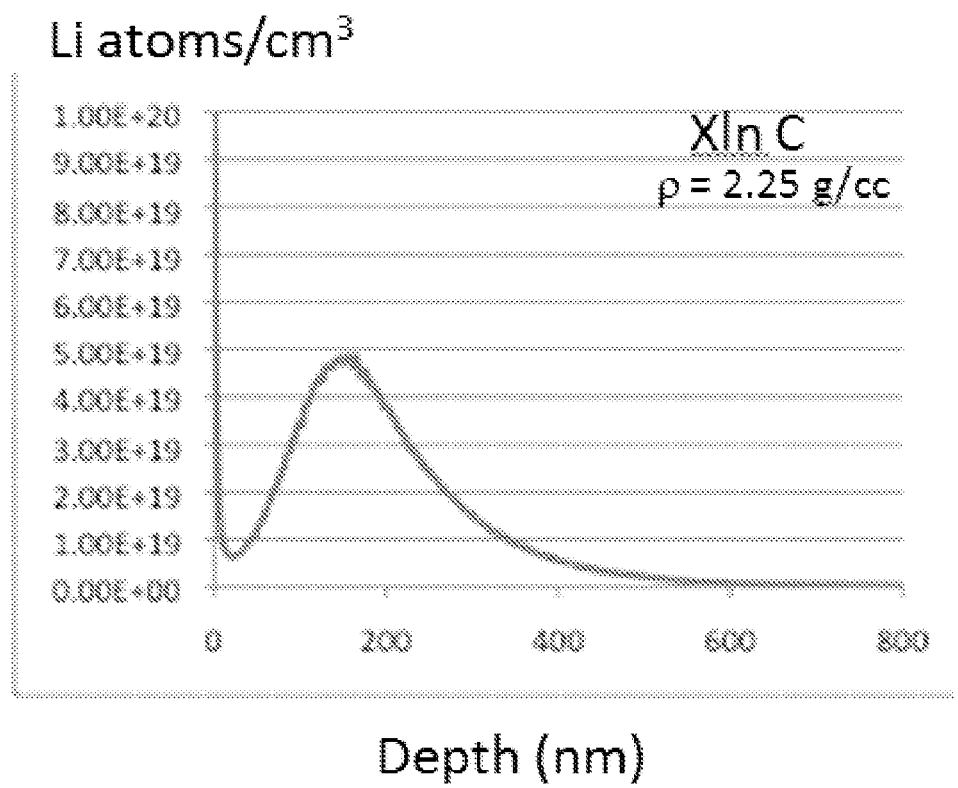
FIG. 7D is a measured lithium implant profile using a single crystal C matrix.
Figure 8A:
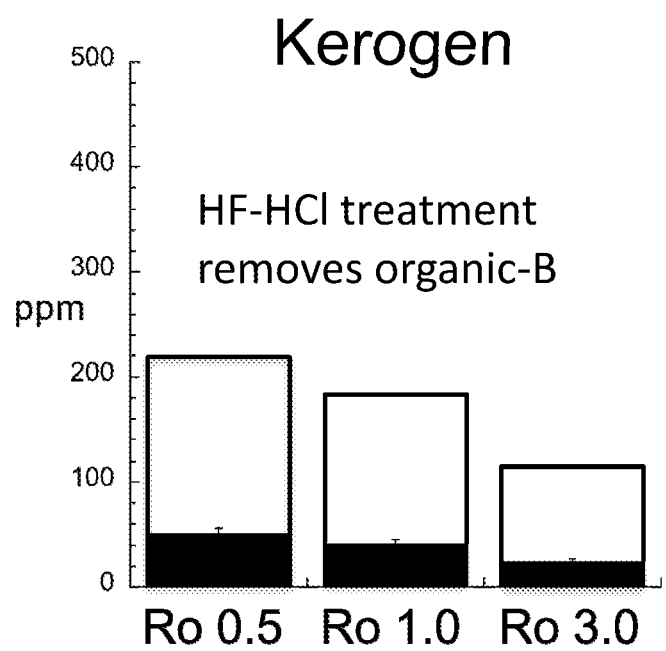
FIG. 8A shows the boron content of the kerogen in immature (left), mature (center), and overmature (right) Bakken shale. NanoSIMS measurements indicate that B is lost during isolation of kerogen using HF-HCL. Black shows B in kerogen after HF-HCL extraction, white shows B in kerogen with no chemical treatment (measured directly by NanoSIMS).
Figure 8B:
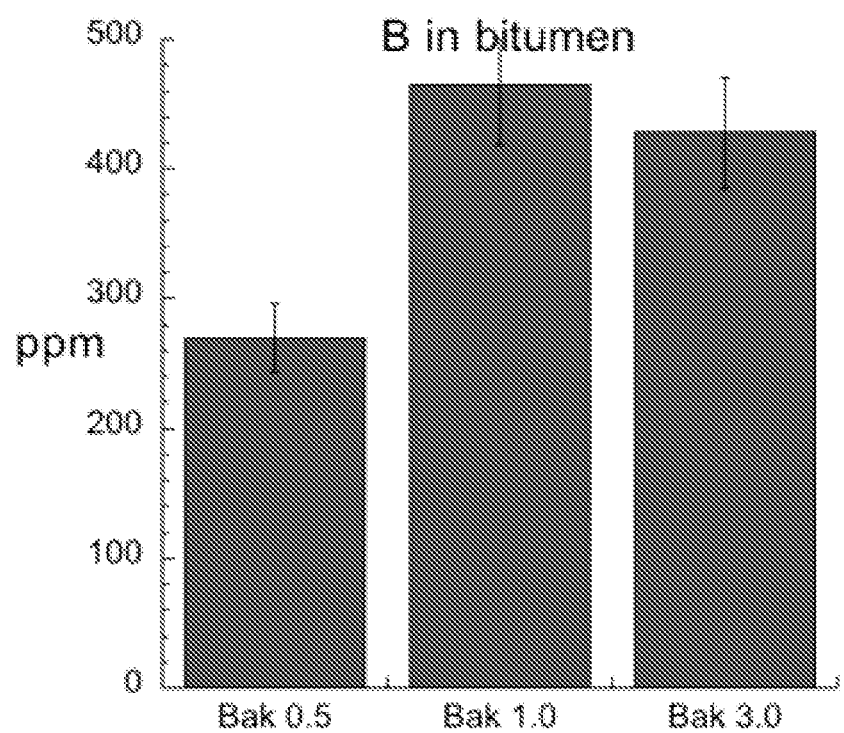
FIG. 8B shows the boron content of the bitumen in immature (left), mature (center), and overmature (right) Bakken shale.
Figure 8C:
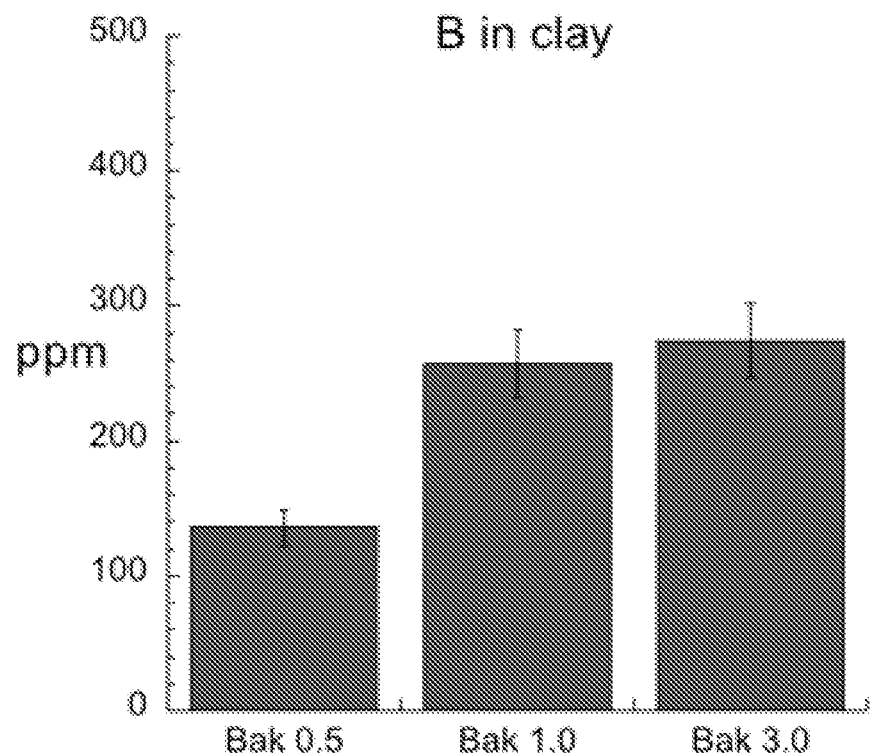
FIG. 8C shows the boron content of the clay in immature (left), mature (center), and overmature (right) Bakken shale.
Figure 8D:
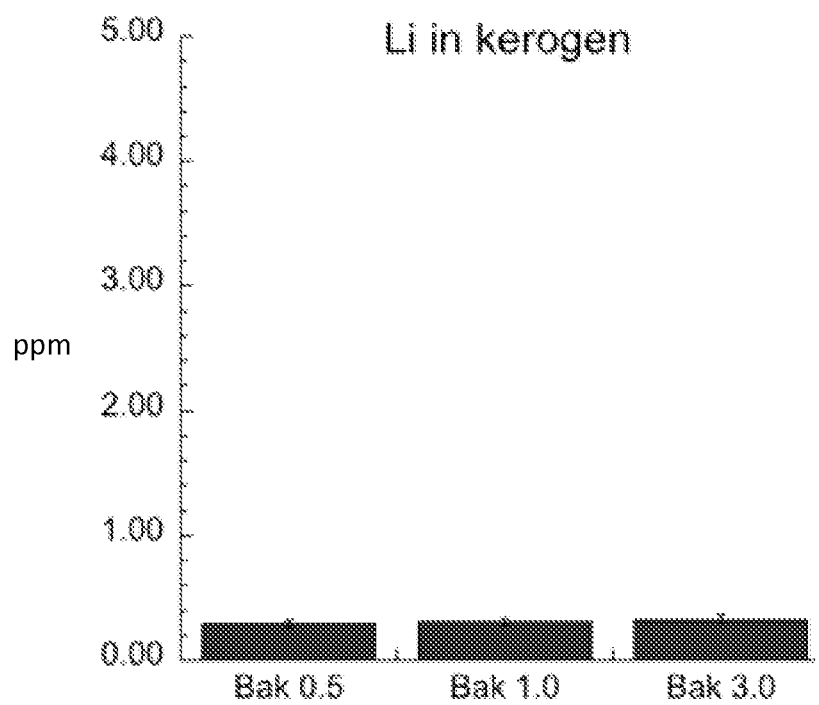
FIG. 8D shows the lithium content of the kerogen in immature (left), mature (center), and overmature (right) Bakken shale.
Figure 8E:
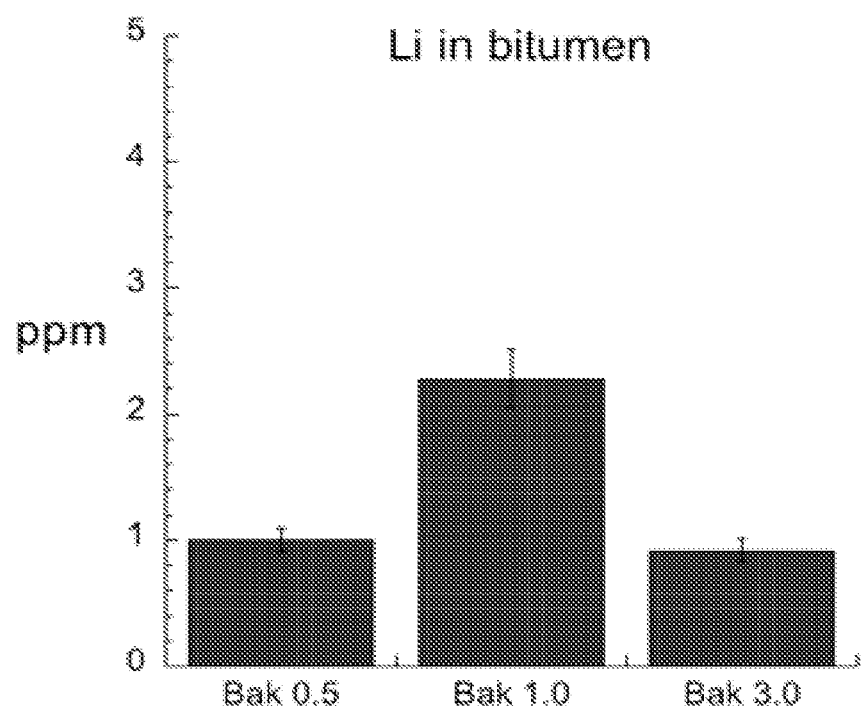
FIG. 8E shows the lithium content of the bitumen in immature (left), mature (center), and overmature (right) Bakken shale.
Figure 8F:
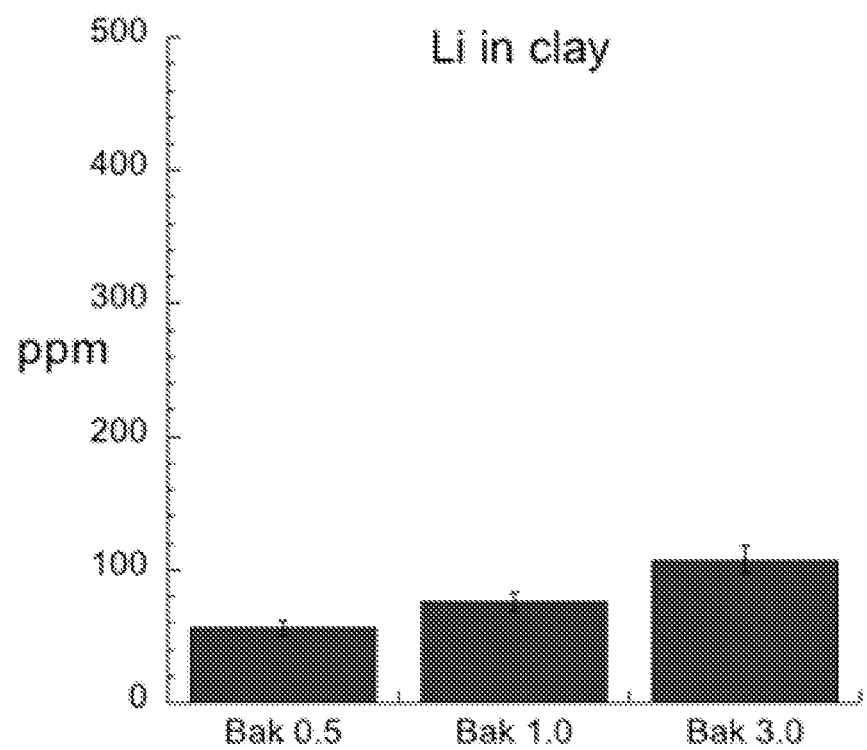
FIG. 8F shows the lithium content of the clay in immature (left), mature (center), and overmature (right) Bakken shale.

FIG. 6 is an example showing counts of the ion of interest over time (cps), which correlates with depth in Å. The ion yield over time for each matrix and isotope was converted to a relative sensitivity factor (RSF), which allows the calibration for converting ion counts to ppm. Specifically, integrating the cps for each matrix allows the calculation of the RSF, where RSF=(dose/crater depth)×(matrix cps/ion cps) for each matrix. This value in atoms/cm$^3$ is then converted to ppm, using Avogadro's number, the matrix density, and molar mass for the element. The results, which shows little matrix effect on RSFs for B, but much bigger differences for Li, are shown in Table 1 below.

TABLE 1

RSF and ppm for three different matrices

| Implant Matrix | RSF (ions/cm3) | | Sputter rate (Å/s) | Density g/cc |
| --- | --- | --- | --- | --- |
| | 7Li | 11B | | |
| NIST 612 (30Si) | 3.15E+20 | 1.15E+21 | 1 | 2.52 |
| Glassy C (12C) | 1.25E+18 | 2.25E+20 | 2 | 1.5 |
| Xln C (12C) | 1.93E+19 | 1.40E+21 | 2 | 2.5 |

TABLE 1-continued

RSF and ppm for three different matrices

| Implant Matrix | RSF (ions/cm3) | | Sputter rate (Å/s) | Density g/cc |
|---|---|---|---|---|
| | 7Li | 11B | | |
| Bak 0.5 | 2.80E+18 | 1.85E+18 | 5 | 1.25 |
| Bak 1.0 | 1.90E+19 | 3.30E+19 | 5 | 1.35 |
| Bak 3.0 | 1.20E+19 | 3.60E+19 | 5 | 2.25 |

As shown in FIG. 7A-D, the calculated implant profile is not exactly what is measured. The reason for this is that the behaviors of ions in the matrix are different for each element. For example, the Li implants have a long tail compared to the boron implants. While the area under the curve of FIG. 7 can be integrated to determine the calibration in each matrix, the matrix effects on the sputter yield of different organic compounds cannot be determined theoretically; therefore, implants of the ion of interest in each matrix is necessary for accurate calibrations.

Using the new calibrations for B and Li in both silicate and carbon matrices, the inventors can now use these inorganic 'heteroatoms' in kerogen as a tracer of released, fluid mobile hydrocarbons. The isotopic compositions of B and Li were measured by secondary ion mass spectrometry (SIMS) on <2 µm clay fractions, DCM extracted bitumen and HF isolated kerogen.

FIG. 8 shows the results of the B and Li content analysis of the kerogen and bitumen as well as the clay. Vitrinite reflectance was 0.5, 1.0 and 3.0% respectively. It was found that boron in the kerogen is very low relative to the bitumen (FIGS. 8A and 8B), and the B concentration in kerogen decreases with increasing thermal grade (FIG. 8A). Also, bitumen has the highest B in the 'peak oil' sample (FIG. 8B). Clay shows increasing B content with increasing thermal maturity as the clay takes up B released from the kerogen (FIG. 8C).

The Li calibrations were further tested on the observation that those implants indicated a two order of magnitude difference between the calibration in carbon vs. silicate matrices. The trends show increased Li in the bitumen (FIG. 8E) relative to kerogen (FIG. 8D), and increasing Li contents in clays with increasing thermal grade (FIG. 8F), just as is observed for B. It was shown that the lower B contents of the kerogen samples is a result of the kerogen extraction protocol (digestion in HF) which could volatilize B. The same may be true for Li. The NanoSIMS measurement of B in kerogen was used to test this on a small area of kerogen spatially resolved from interfering clays.

Figure 9A:
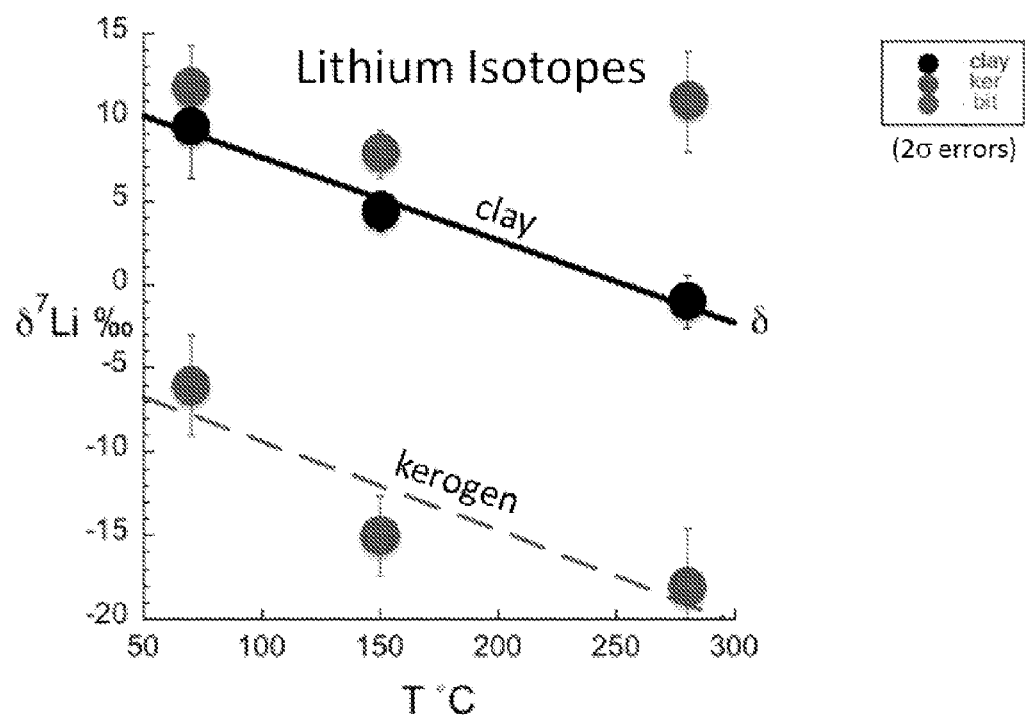
FIG. 9A shows the isotopic composition of lithium in kerogen, clay and bitumen as a function of temperature, as estimated from vitrinite reflectance.
Figure 9B:
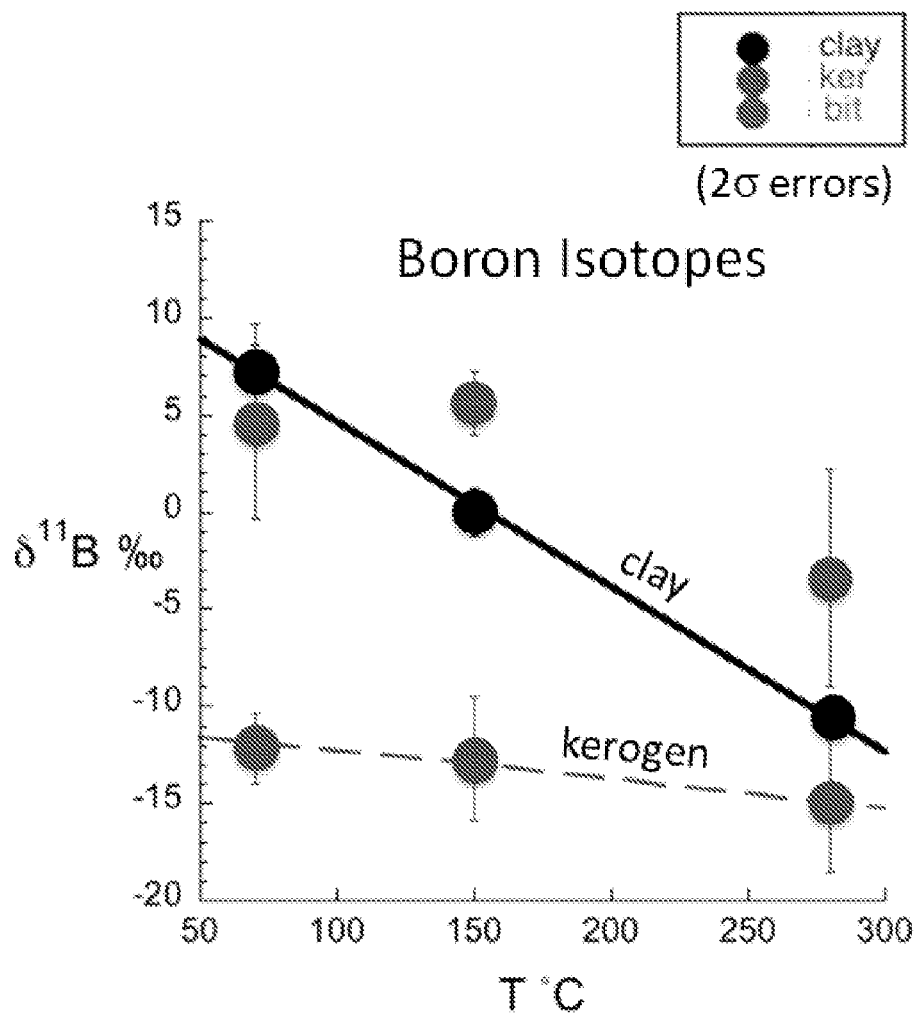
FIG. 9B shows the isotopic composition of boron in kerogen, clay and bitumen as a function of temperature, as estimated from vitrinite reflectance.

FIG. 9 shows the isotopic composition of Li and B in the kerogen, clay and bitumen as a function of temperature estimated from vitrinite reflectance. Results show that the <2 µm clay fraction (organics removed) produces a linear decrease in $\delta^{11}B$ (+7 to −12‰) and $\delta^7Li$ (+10 to −1‰) from immature to overmature shale (1σ errors<1‰) (FIG. 9A). Similar results were observed for B-isotopes (FIG. 9B), although kerogen shows less change with temperature. Specifically, the kerogen $\delta^{11}B$ ranges from (−12 to −15‰) while $\delta^7Li$ decreases (−6 to −18‰) with increasing thermal maturity. These trends suggest kerogen is the source of isotopically light B and Li that substitute in illite during diagenesis. In contrast, bitumen $\delta^{11}B$ averages +3‰ and $\delta^7Li$ averages +10‰, showing no change with kerogen thermal maturity. Thus, there is a linear trend for B and Li isotopes in kerogen and clay with temperature, but no significant change for bitumen, but the bitumen is enriched in the heavy isotope compared to kerogen. No clear trend of bitumen with thermal grade suggests that the bitumen has migrated from a different source after burial produced the thermal gradient.

Knowing isotope fractionation factors for B and Li between illite and water and using the Ro values to estimate temperature, a calculation of the $\delta^{11}B$ and $\delta^7Li$ of water was made assuming equilibrium. This calculation can further be used to estimate the isotope fractionations between the kerogen and water for B and Li as a function of temperature based on the following formulations:

For B: $1000 \ln \alpha_{ker-water} = -23(1000/K)+22$;

For Li: $1000 \ln \alpha_{ker-water} = -8(1000/K)-13$.

Figure 10A:
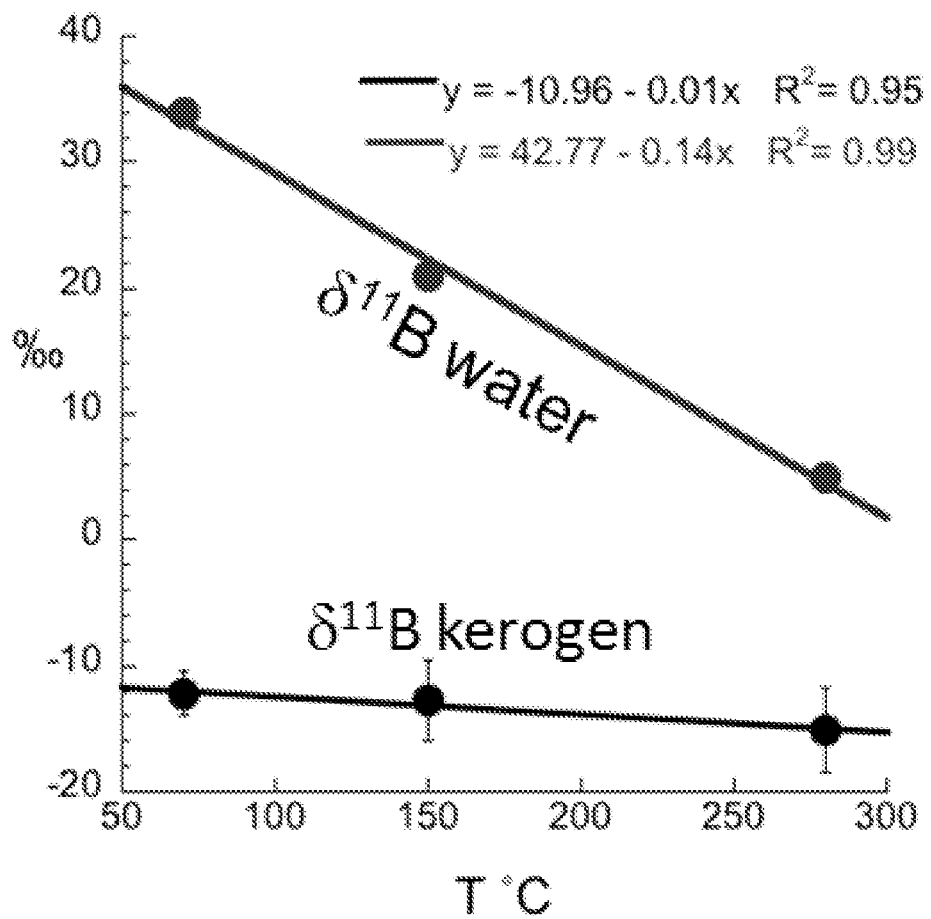
FIG. 10A shows the isotopic variation of boron in water and kerogen as a function of temperature.
Figure 10B:
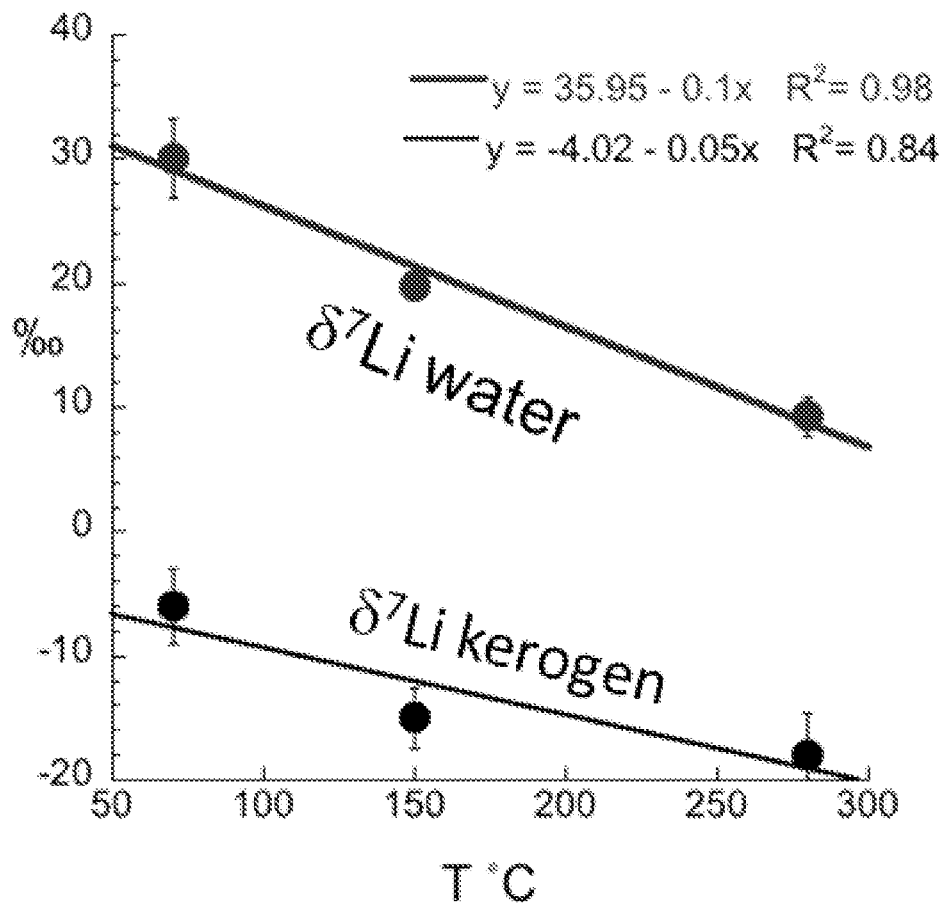
FIG. 10B shows the isotopic variation of lithium in water and kerogen as a function of temperature.

As shown in FIG. 10, there is a 30‰ range in B-isotope fractionation as B is released from kerogen over a temperature range of ~70-280° C. (FIG. 10A), while Li-isotope fractionation changes by ~10% (FIG. 10B). The large isotope fractionations over temperatures of hydrocarbon generation make B and Li released from kerogen a viable tracer of mature hydrocarbon related fluids (water and bitumen). It is further found that for Li, the clay and kerogen fractionation slopes are similar, with kerogen about 7‰ enriched in the lighter isotope (FIG. 10B). For B, the fractionation is not parallel (FIG. 10A). The slope for kerogen is more than two times steeper than clay and equivalent to the clay-water fractionation at about 150° C.

Figure 10C:
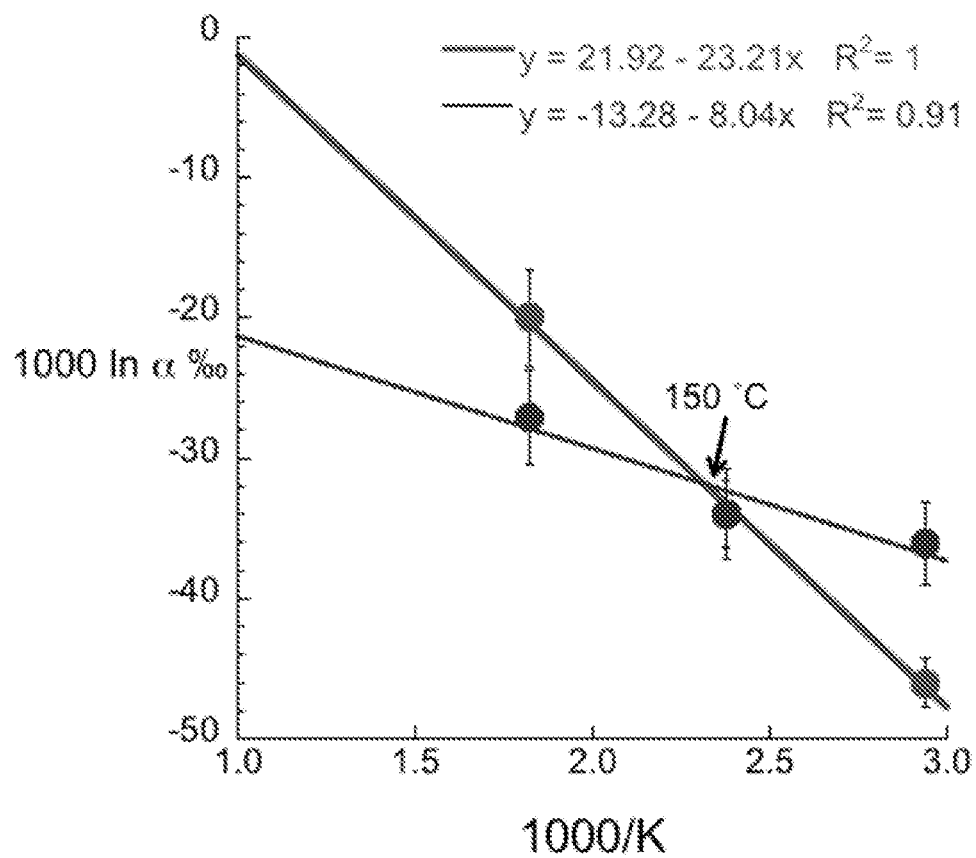
FIG. 10C shows the empirical isotope fractionation of boron (red) and lithium (blue) between kerogen and water in the Bakken shale samples studied.
Figure 11:
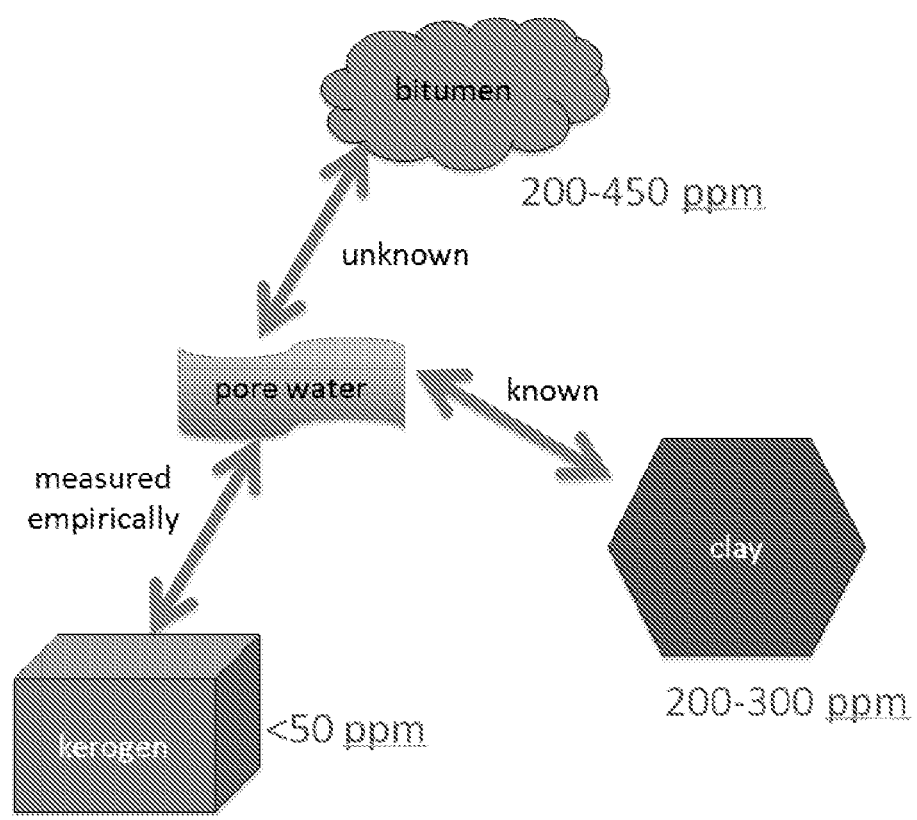
FIG. 11 is a schematic diagram illustrating how knowing the isotope fractionation factors for boron and lithium between kerogen-water, clay-water and bitumen-water can allow determination of the source of hydrocarbons in nanoporous kerogen from oil shales.

Thus, the kerogen-water fractionation with temperature can be estimated by using a water composition based on the established clay-water fractionation curve (FIG. 10C). It is clear that the bitumen has concentrated the heavier isotopes of B and Li. It can be further envisioned that if kerogen is the sole source (or predominant source) of the trace elements then about ten times the volume of kerogen is needed to produce the measured bitumen B and Li content (FIG. 11). This estimated correlation suggests that B and Li are useful tracers of migrated hydrocarbons in nanoporous kerogen from oil shales. Elevated concentrations of B and Li in shale nanopores may help to identify optimal targets for enhanced oil recovery.

Thus, the invention provides methods for determining the source of hydrocarbons and their by-products in an oil reservoir rock, and more particularly, the source of hydrocarbons presented in the pores of kerogen.

Each of the publications cited in this application is incorporated by herein in its entirety. Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A method for identifying the source of hydrocarbons within the pores of a host rock, the method comprising:
    (a) determining a first isotopic composition of boron or lithium in one or more components within a potential source rock sample selected from the group consisting of kerogen, clay, and water;
    (b) determining a second isotopic composition of the same boron or lithium in the hydrocarbons within the pores of a host rock sample; and
    (c) comparing the first and second isotopic compositions to determine whether the potential source rock is the source of the hydrocarbons within the pores of the host rock.

2. The method of claim 1, wherein the host rock comprises kerogen, and wherein the pores of the host rock sample are pores within the kerogen of the host rock sample.

3. The method of claim 2, wherein the host rock sample and the potential source rock sample are the same, and whereby the method determines whether the bitumen within the host rock is the source of the hydrocarbons within the pores of the host rock.

4. The method of claim 1, wherein the comparison step (c) comprises using a relationship between the first isotopic composition and a third isotopic composition of boron or lithium within the bitumen phase of the potential source rock.

5. The method of claim 4, wherein the potential source rock is identified as the source of the hydrocarbons within the pores of the host rock if the third isotopic composition is substantially similar to the second isotopic composition.

6. The method of claim 4, further comprising measuring the thermal maturity of the kerogen within the potential source rock sample, wherein the relationship between the first isotopic composition and the third isotopic composition is based in part on the thermal maturity of the kerogen within the potential source rock.

7. The method of claim 4, wherein the relationship between the first isotopic composition and the third isotopic composition is based at least in part on the boron isotope or lithium isotope fractionation between one or more of:
  (a) the kerogen and bitumen within the potential source rock;
  (b) the clay and bitumen within the potential source rock; or
  (c) the water and bitumen within the potential source rock.

8. The method of claim 7, wherein the relationship between the first isotopic composition and the third isotopic composition is further based at least in part on the boron isotope or lithium isotope fractionation between one or more of:
  (d) the clay and water within the potential source rock; or
  (e) the kerogen and water within the potential source rock.

9. The method of claim 4, wherein the relationship between the first isotopic composition and the third isotopic composition is based at least in part on an isotope fractionation curve or an isotope fractionation equation.

10. The method of claim 1, further comprising the step of using the identified source of the hydrocarbons in the pores of the host rock to determine whether to extract hydrocarbons from the host rock.

11. The method of claim 10, further comprising the step of extracting hydrocarbons from the host rock.

12. The method of claim 11, wherein the step of extracting hydrocarbons from the source rock comprises drilling into the host rock or hydrofracturing the host rock.

13. The method of claim 1, wherein the host rock is a black shale, an oil shale, or a gas shale.

14. The method of claim 6, wherein the step of measuring the thermal maturity of the kerogen within the potential source rock sample is performed by determining vitrinite reflectance or by using other thermal indicators.

15. The method of claim 1, wherein step (a), step (b), or both are performed using mass spectrometry.

16. The method of claim 15, wherein the mass spectrometry used to perform step (a), step (b), or both is nano secondary ion mass spectrometry (NanoSIMS).

17. A method for identifying a source of hydrocarbon contaminants in groundwater, the method comprising:
  (a) determining a first isotopic composition of boron or lithium in one or more components within a potential source rock sample selected from the group consisting of kerogen, clay, and water;
  (b) determining a second isotopic composition of the same boron or lithium within the hydrocarbon contaminants in groundwater; and
  (c) comparing the first and second isotopic compositions to determine if the source rock is the source of the hydrocarbon contaminants.

18. The method of claim 17, wherein potential source rock comprises oil shale.

19. The method of claim 17, wherein the comparison step (c) comprises using a relationship between the first isotopic composition and a third isotopic composition of boron or lithium within the bitumen phase of the potential source rock.

20. The method of claim 17, wherein the relationship between the first isotopic composition and the third isotopic composition is based at least in part on the boron isotope or lithium isotope fractionation between one or more of:
  (a) the kerogen and bitumen within the potential source rock;
  (b) the clay and bitumen within the potential source rock; or
  (c) the water and bitumen within the potential source rock.

* * * * *